(12) United States Patent
Wolfe et al.

(10) Patent No.: US 10,448,872 B2
(45) Date of Patent: Oct. 22, 2019

(54) ANALYTE SENSOR APPARATUSES HAVING IMPROVED ELECTRODE CONFIGURATIONS AND METHODS FOR MAKING AND USING THEM

(75) Inventors: Katherine T. Wolfe, Dunwoody, GA (US); Ameya S. Kantak, Encino, CA (US); Eric Allan Larson, Simi Valley, CA (US); Daniel E. Pesantez, Canoga Park, CA (US); Dongjuan Xi, San Marcos, CA (US); Chia-Hung Chiu, Granada Hills, CA (US); Rajiv Shah, Rancho Palos Verdes, CA (US)

(73) Assignee: MEDTRONIC MINIMED, INC., Northridge, CA (US)

(*) Notice: Subject to any disclaimer, the term of this patent is extended or adjusted under 35 U.S.C. 154(b) by 2402 days.

(21) Appl. No.: 13/047,431

(22) Filed: Mar. 14, 2011

(65) Prior Publication Data
US 2011/0230735 A1    Sep. 22, 2011

Related U.S. Application Data

(60) Provisional application No. 61/314,484, filed on Mar. 16, 2010.

(51) Int. Cl.
*A61B 5/1486* (2006.01)
*A61B 5/145* (2006.01)
*A61B 5/00* (2006.01)

(52) U.S. Cl.
CPC ...... *A61B 5/14865* (2013.01); *A61B 5/14503* (2013.01); *A61B 5/14532* (2013.01); *A61B 5/14542* (2013.01); *A61B 5/14546* (2013.01); *A61B 5/6848* (2013.01)

(58) Field of Classification Search
CPC . A61B 5/14532; A61B 5/1468; A61B 5/1473; A61B 5/1486; A61B 5/14865
USPC ....... 600/345, 347, 365, 372, 373, 381, 382, 600/391, 395; 204/403, 412
See application file for complete search history.

(56) References Cited

U.S. PATENT DOCUMENTS

| | | | |
|---|---|---|---|
| 4,114,627 | A | 9/1978 | Lewyn et al. |
| 4,373,531 | A | 2/1983 | Wittkampf et al. |
| 4,402,819 | A | 9/1983 | Rechnitz et al. |
| 4,431,004 | A | 2/1984 | Bessman et al. |
| 4,562,751 | A | 1/1986 | Nason et al. |
| 4,573,994 | A | 3/1986 | Fischell |
| 4,678,408 | A | 7/1987 | Nason et al. |

(Continued)

FOREIGN PATENT DOCUMENTS

| | | |
|---|---|---|
| CN | 101454667 | 6/2009 |
| EP | 1 153 571 | 11/2001 |

(Continued)

OTHER PUBLICATIONS

PCT International Search Report and Written Opinion dated Jun. 28, 2011 (PCT/US2011/028447).

(Continued)

*Primary Examiner* — Meredith Weare
(74) *Attorney, Agent, or Firm* — Gates & Cooper LLP

(57) ABSTRACT

Embodiments of the invention provide analyte sensors having optimized elements and/or configurations of elements as well as methods for making and using such sensors. Typical embodiments of the invention include glucose sensors used in the management of diabetes.

23 Claims, 13 Drawing Sheets

(56) References Cited

U.S. PATENT DOCUMENTS

| | | | |
|---|---|---|---|
| 4,685,903 | A | 8/1987 | Cable et al. |
| 4,703,756 | A | 11/1987 | Gough et al. |
| 4,858,610 | A | 8/1989 | Callaghan et al. |
| 4,890,620 | A | 1/1990 | Gough |
| 4,894,253 | A | 1/1990 | Heineman et al. |
| 4,991,583 | A | 2/1991 | Silvian |
| 5,149,630 | A | 9/1992 | Forrest et al. |
| 5,165,407 | A | 11/1992 | Wilson et al. |
| 5,170,806 | A | 12/1992 | Colen |
| 5,212,050 | A | 5/1993 | Mier et al. |
| 5,299,571 | A | 4/1994 | Mastrototaro |
| 5,320,725 | A | 6/1994 | Gregg et al. |
| 5,390,671 | A | 2/1995 | Lord et al. |
| 5,390,691 | A | 2/1995 | Sproule et al. |
| 5,391,250 | A | 2/1995 | Cheney, II et al. |
| 5,427,912 | A | 6/1995 | Brown et al. |
| 5,482,473 | A | 1/1996 | Lord et al. |
| 5,486,201 | A | 1/1996 | Canfield |
| 5,494,562 | A | 2/1996 | Maley et al. |
| 5,497,772 | A * | 3/1996 | Schulman et al. ............ 600/347 |
| 5,568,806 | A | 10/1996 | Chekney, II et al. |
| 5,586,553 | A * | 12/1996 | Halili et al. ................. 600/316 |
| 5,605,152 | A | 2/1997 | Slate et al. |
| 5,705,399 | A | 1/1998 | Larue |
| 5,755,939 | A | 5/1998 | Dror et al. |
| 5,771,868 | A | 6/1998 | Khair |
| 5,777,060 | A | 7/1998 | Van Antwerp et al. |
| 5,786,439 | A | 7/1998 | Van Antwerp et al. |
| 5,882,494 | A | 3/1999 | Van Antwerp et al. |
| 5,981,203 | A | 11/1999 | Meyerhoff et al. |
| 5,985,129 | A | 11/1999 | Gough et al. |
| 6,001,067 | A | 12/1999 | Shults et al. |
| 6,119,028 | A | 9/2000 | Schulman et al. |
| 6,120,676 | A | 9/2000 | Heller et al. |
| 6,122,536 | A | 9/2000 | Sun et al. |
| 6,141,573 | A | 10/2000 | Kurnik et al. |
| 6,155,992 | A | 12/2000 | Henning et al. |
| 6,212,416 | B1 | 4/2001 | Ward et al. |
| 6,270,637 | B1 * | 8/2001 | Crismore et al. ........ 204/403.04 |
| 6,319,540 | B1 | 11/2001 | Van Antwerp et al. |
| 6,368,274 | B1 | 4/2002 | Van Antwerp et al. |
| 6,400,974 | B1 | 6/2002 | Lesho |
| 6,410,251 | B2 | 6/2002 | Hoshino et al. |
| 6,413,393 | B1 | 7/2002 | Van Antwerp et al. |
| 6,512,939 | B1 | 1/2003 | Colvin et al. |
| 6,514,718 | B2 | 2/2003 | Heller et al. |
| 6,542,765 | B1 | 4/2003 | Guy et al. |
| 6,551,276 | B1 | 4/2003 | Mann et al. |
| 6,558,351 | B1 | 5/2003 | Steil et al. |
| 6,595,919 | B2 | 7/2003 | Berner et al. |
| 6,661,275 | B2 | 12/2003 | Logiudice |
| 6,702,857 | B2 | 3/2004 | Brauker et al. |
| 6,703,210 | B2 | 3/2004 | Egashira |
| 6,706,159 | B2 | 3/2004 | Moerman et al. |
| 6,770,729 | B2 | 8/2004 | Van Antwerp |
| 7,081,195 | B2 | 7/2006 | Simpson et al. |
| 7,278,893 | B1 | 10/2007 | Ireland et al. |
| 7,318,816 | B2 | 1/2008 | Bobroff et al. |
| 7,344,500 | B2 | 3/2008 | Talbot et al. |
| 7,455,663 | B2 | 11/2008 | Bikovsky |
| 7,686,787 | B2 | 3/2010 | Moberg et al. |
| 8,660,628 | B2 | 2/2014 | Wang et al. |
| 8,700,114 | B2 | 4/2014 | Gottlieb et al. |
| 2002/0022855 | A1 | 2/2002 | Bobroff et al. |
| 2002/0090738 | A1 | 7/2002 | Cozzette et al. |
| 2004/0002682 | A1 | 1/2004 | Kovelman et al. |
| 2005/0115832 | A1 | 6/2005 | Simpson et al. |
| 2005/0161346 | A1 | 7/2005 | Simpson et al. |
| 2006/0076236 | A1 * | 4/2006 | Shah et al. .............. 204/403.01 |
| 2006/0195148 | A1 | 8/2006 | Norton et al. |
| 2007/0213611 | A1 * | 9/2007 | Simpson et al. ............. 600/365 |
| 2007/0235331 | A1 | 10/2007 | Simpson et al. |
| 2008/0128265 | A1 * | 6/2008 | O'Hare et al. ................ 204/155 |
| 2008/0135408 | A1 * | 6/2008 | Sjolander ................ 204/403.01 |
| 2008/0275313 | A1 * | 11/2008 | Brister et al. ................ 600/300 |
| 2008/0314753 | A1 * | 12/2008 | Zhou ............................ 205/112 |
| 2010/0025238 | A1 * | 2/2010 | Gottlieb et al. ............. 204/401 |
| 2010/0192369 | A1 * | 8/2010 | Hodges et al. ................. 29/825 |
| 2010/0331643 | A1 * | 12/2010 | Mazza et al. ................ 600/345 |
| 2010/0331644 | A1 * | 12/2010 | Neale et al. ................. 600/345 |
| 2011/0082356 | A1 | 4/2011 | Yang et al. |

FOREIGN PATENT DOCUMENTS

| | | |
|---|---|---|
| JP | 2002-537634 | 11/2002 |
| JP | 2009-519106 | 5/2009 |
| WO | WO 00/018449 | 4/2000 |
| WO | WO 00/019887 | 4/2000 |
| WO | WO 01/058348 | 8/2001 |
| WO | WO 03/022128 | 3/2003 |
| WO | WO 03/022352 | 3/2003 |
| WO | WO 03/023388 | 3/2003 |
| WO | WO 03/023708 | 3/2003 |
| WO | WO 03/034902 | 5/2003 |
| WO | WO 03/035117 | 5/2003 |
| WO | WO 03/035891 | 5/2003 |
| WO | WO 03/036255 | 5/2003 |
| WO | WO 03/036310 | 5/2003 |
| WO | WO 03/074107 | 9/2003 |
| WO | WO 04/008956 | 1/2004 |
| WO | WO 04/009161 | 1/2004 |
| WO | WO 04/021877 | 3/2004 |
| WO | 2008017645 | 2/2008 |
| WO | WO 08/042625 | 4/2008 |

OTHER PUBLICATIONS

Bruckel et al., "In Vivo Measurement of Subcutaneous Glucose Concentrations with an Enzymatic Glucose Sensor and a Wick Method", Klin. Wochenschr, 1989, 67: 491-495.

Choi et al., "Amperometric biosensors employing an insoluble oxidant as an interference-removing agent". Analytica Chemica Acta 461 (2002): 251-260.

Lowe, "Biosensors". Trends in Biotechnology, vol. 2, No. 3, 1984: pp. 59-65.

Murakami et al., "A Micro Planar Ampehometric Glucose Sensor Using an Isfet as a Reference Electrode", Analytical Letters, 1986, 19(19-20): 1973-1986.

Pickup et al., "In vivo molecular sensing in diabetes mellitus: an implantable glucose sensor with direct electron transfer", Diabetologia , 1989, 32(3): 213-217.

Shichiri et al., "In vivo characteristics of needle-type glucose sensor—measurements of subcutaneous glucose concentrations in human volunteers", Hormone and metabolic research, Supplement series, 1987, 20: 17-20.

Taylor, "Protein Immobilization: Fundamentals and Applications". Bioprocess Technology, vol. 14, 1991: 19 pages.

Yao, "A chemically-modified enzyme membrane electrode as an amperometric glucose sensor", Analytica Chimica Acta, 1983, 148: 27-33.

* cited by examiner

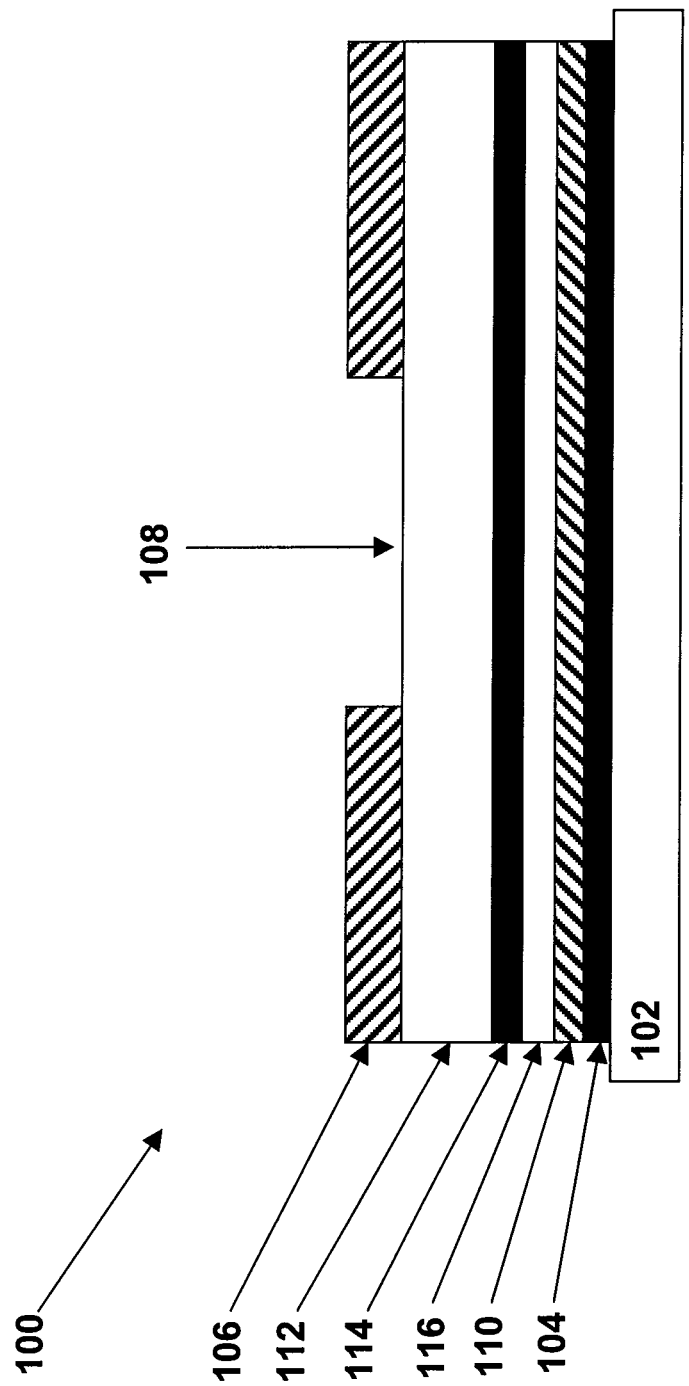

ANALYTE SENSOR APPARATUSES HAVING IMPROVED ELECTRODE CONFIGURATIONS AND METHODS FOR MAKING AND USING THEM

CROSS REFERENCE TO RELATED APPLICATIONS

This application is related to U.S. patent application Ser. No. 12/184,046; U.S. patent application Ser. No. 10/861,837, U.S. patent application Ser. No. 11/149,119, U.S. patent application Ser. No. 11/301,512, U.S. patent application Ser. No. 11/397,543, U.S. patent application Ser. No. 11/492,273, U.S. patent application Ser. No. 11/897,106, U.S. patent application Ser. No. 11/966,294, and U.S. patent application Ser. No. 11/323,242, the contents of each of which are incorporated herein by reference. This application claims the benefit under 35 USC § 119(e) to U.S. Provisional Patent Application No. 61/314,484, filed on Mar. 16, 2010, the contents of which are incorporated herein by reference.

BACKGROUND OF THE INVENTION

1. Field of the Invention

Analyte sensors (e.g. glucose sensors used in the management of diabetes) and methods and materials for making and using such sensors.

2. Description of Related Art

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

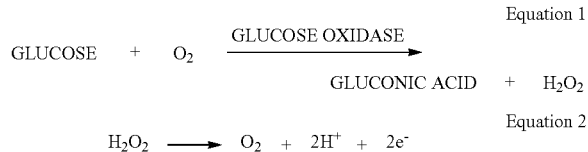

$$\text{GLUCOSE} + O_2 \xrightarrow{\text{GLUCOSE OXIDASE}} \text{GLUCONIC ACID} + H_2O_2 \quad \text{Equation 1}$$

$$H_2O_2 \longrightarrow O_2 + 2H^+ + 2e^- \quad \text{Equation 2}$$

The glucose oxidase is used to catalyze the reaction between glucose and oxygen to yield gluconic acid and hydrogen peroxide (equation 1). The $H_2O_2$ reacts electrochemically as shown in equation 2, and the current can be measured by a potentiostat. These reactions, which occur in a variety of oxidoreductases known in the art, are used in a number of sensor designs.

As analyte sensor technology matures and new applications for sensor technology are developed, there is a need for methods and materials that facilitate the use of sensors in the wide variety of situations in which the measurement of an analyte is desirable.

SUMMARY OF THE INVENTION

Embodiments of the invention disclosed herein include analyte sensors and sensor systems such as amperometric glucose sensors used in the management of diabetes as well as optimized methods for monitoring analytes using such sensors and sensor systems. One embodiment of the invention is an analyte sensor comprising: an analyte sensor comprising a plurality of sensor wires having a first end and second end and each arranged in a substantially common orientation, the plurality of sensor wires being electrically conductive and including a first sensor wire substantially covered by a first electrically insulating cover, wherein an aperture in the first electrically insulating cover defines a working electrode area, a second sensor wire substantially covered by a second electrically insulating cover, wherein an aperture in the second electrically insulating cover defines a reference electrode area, and a third sensor wire substantially covered by a third electrically insulating cover, wherein an aperture in the third electrically insulating cover defines a counter electrode area. In further embodiments, there are additional wires also arranged in a substantially common orientation. The additional wires may also have electrically insulating covers with apertures defining further electrodes. For example, there may be an additional wire with a second counter electrode.

In further embodiments, the plurality of sensor wires are arranged in a ribbon wire configuration. In other embodiments, the plurality of sensor wires are arranged in a bundled configuration. In other embodiments, the plurality of sensor wires are arranged in a stacked configuration. In further embodiments, the plurality of sensor wires may be coiled around a core cylindrical material. The core cylindrical material may be made of a suitable biocompatible material. Examples of such materials include coated polymers, hydrogels and shape memory alloys.

In further embodiments, one or more of the plurality of wires has second aperture in its electrically insulating cover defining a second electrode area. In still further embodiments, each of the plurality of wires has two ore more electrode areas defined in its electrically insulating cover, such that the electrode areas are distributed along an implantable portion of the sensor apparatus. In further embodiments, the working electrode area is on the opposite side of the plurality of wires from the counter and reference electrode areas.

In further embodiments, the first and third sensor wires each comprise a material independently selected from the group consisting of platinum, iridium, iridium oxide, and palladium. In further embodiments, the second sensor wire comprises a material selected from the group consisting of silver, silver chloride, and a combination of silver and silver chloride. In further embodiments the electrically insulating covers each comprise a material independently selected from the group consisting of PTFE (polytetrafluoroethylene), ETFE (ethylene tetrafluoroethylene), FEP (fluorinated ethylene propylene), and PFA (perfluoroalkoxy). In further embodiments, at least one of the plurality of sensor wires comprises a shape memory alloy.

In embodiments of the present invention, the portion of the first sensor wire exposed at the working electrode area is coated with an electrode coating selected from the group consisting of platinum black, porous platinum, iridium, iridium oxide, and polypyrrole. The portion of the first sensor wire exposed at the working electrode area may be modified to increase surface area. The portion of the first sensor wire exposed at the working electrode area may be at least partially coated with one or more components selected from the group consisting of porous metals and porous polymers.

In embodiments of the present invention, chemical layers may be added over electrode areas, for example the working electrode area. For example, the portion of the first wire exposed at the working electrode area may be coated with an analyte sensing layer, such as glucose oxidase. The analyte sensing layer may be coated with an analyte modulating layer, such as a layer comprising PDMS. In between the two layers may be an adhesion promoting layer, such as a layer comprising a silane compound. In further embodiments, a protein layer may be added as well.

In embodiments of the present invention, at least one of the plurality of sensor wires has a second aperture in its electrically insulating cover defining a second electrode area. In further embodiments, the plurality of sensor wires has a first side and a second side opposite to the first side, and wherein the working electrode area is on the first side and the counter electrode area and reference electrode areas are on the second side. In still further embodiments, each of the plurality of sensor wires has a tip at the first end of the plurality of sensor wires, wherein the tips are not covered by the electrically insulating covers, and wherein the tips are coated by a tipping layer. The tipping layer may comprise a poly(p-xylylene) polymer.

In further embodiments, each of the plurality of sensor wires is exposed from the electrically insulating cover at a portion defining a contact in electrical communication with the electrode area on that wire, wherein the contacts are substantially near or at the second end of the plurality of sensor wires and the electrode areas are substantially near or at the first end of the plurality of sensor wires.

Embodiments of the invention disclosed herein include a sensor set comprising a mounting base adapted to be placed on to the skin of a patient, the base including an opening and a connector portion, an analyte sensor comprising a plurality of sensor wires having a first end and second end and each arranged in a substantially common orientation, the plurality of sensor wires being electrically conductive and including a first sensor wire substantially covered by a first electrically insulating cover, wherein an aperture in the first electrically insulating cover defines a working electrode area, a second sensor wire substantially covered by a second electrically insulating cover, wherein an aperture in the second electrically insulating cover defines a reference electrode area, and a third sensor wire substantially covered by a third electrically insulating cover, wherein an aperture in the third electrically insulating cover defines a counter electrode area, wherein the analyte sensor is housed in the mounting base, and wherein near or at its second end each of the plurality of sensor wires is exposed from its electrically insulating cover to define a contact in electrical communication with the connector portion of the base, wherein at least the first end of the analyte sensor extends out of the opening in the mounting base substantially at an angle of ninety degrees from the base. In further embodiments, the sensor set comprises a cannula substantially covering the portion of the analyte sensor extending out of the base.

In further embodiments of the present invention, the sensor set comprises a transmitter connectable to the mounting base at the connector portion and adapted to receive signals from the analyte sensor. The transmitter may include a transmitter recess and transmitter pins inside the recess to electrically connect the transmitter to the analyte sensor when the connecting portion of the mounting base is inserted into the transmitter recess. The connector portion of the mounting base may include stamped conductive pins in electric communication with the electrode areas on the analyte sensor, wherein the stamped conductive pins adapted to connect to the transmitter pins.

In further embodiments, each of the plurality of sensor wires is exposed from the electrically insulating cover at a portion defining a contact in electrical communication with the electrode area on that wire, wherein the contacts are substantially near or at the second end of the plurality of sensor wires and the electrode areas are substantially near or at the first end of the plurality of sensor wires, and wherein the contacts are adapted to electrically connect to the stamped conductive pins. In other embodiments, the mounting base further includes a metal insert adapted to pierce the electrically insulating cover of each of the plurality of electrically conductive wires when the analyte sensor is housed in the mounting base such that the electrode areas are in electronic communication with the metal insert, wherein the metal insert is adapted to electrically connect to the stamped conductive pins.

In further embodiments, a method for avoiding tissue trauma at a sensor insertion site is disclosed, comprising inserting an analyte sensor into the skin of a patient, wherein the analyte sensor includes a plurality of sensor wires having a first end and second end and each arranged in a substantially common orientation, the plurality of sensor wires being electrically conductive and including a first sensor wire substantially covered by a first electrically insulating cover, wherein an aperture in the first electrically insulating cover defines a working electrode area, a second sensor wire substantially covered by a second electrically insulating cover, wherein an aperture in the second electrically insulating cover defines a reference electrode area, and a third sensor wire substantially covered by a third electrically insulating cover, wherein an aperture in the third electrically insulating cover defines a counter electrode area.

Typical embodiments of the invention are comprised of biocompatible materials and/or have structural elements and organizations of elements designed for implantation within a mammal. Methodological embodiments of the invention include methods for making and using the sensor embodiments disclosed herein. Certain embodiments of the invention include methods of using a specific sensor element and/or a specific constellation of sensor elements to produce and/or facilitate one or more properties of the sensor embodiments disclosed herein (e.g. sensor initialization and start-up).

BRIEF DESCRIPTION OF THE FIGURES

FIG. 2A provides a diagrammatic view of a typical layered analyte sensor configuration.

DETAILED DESCRIPTION OF THE EMBODIMENTS

Figure 1:
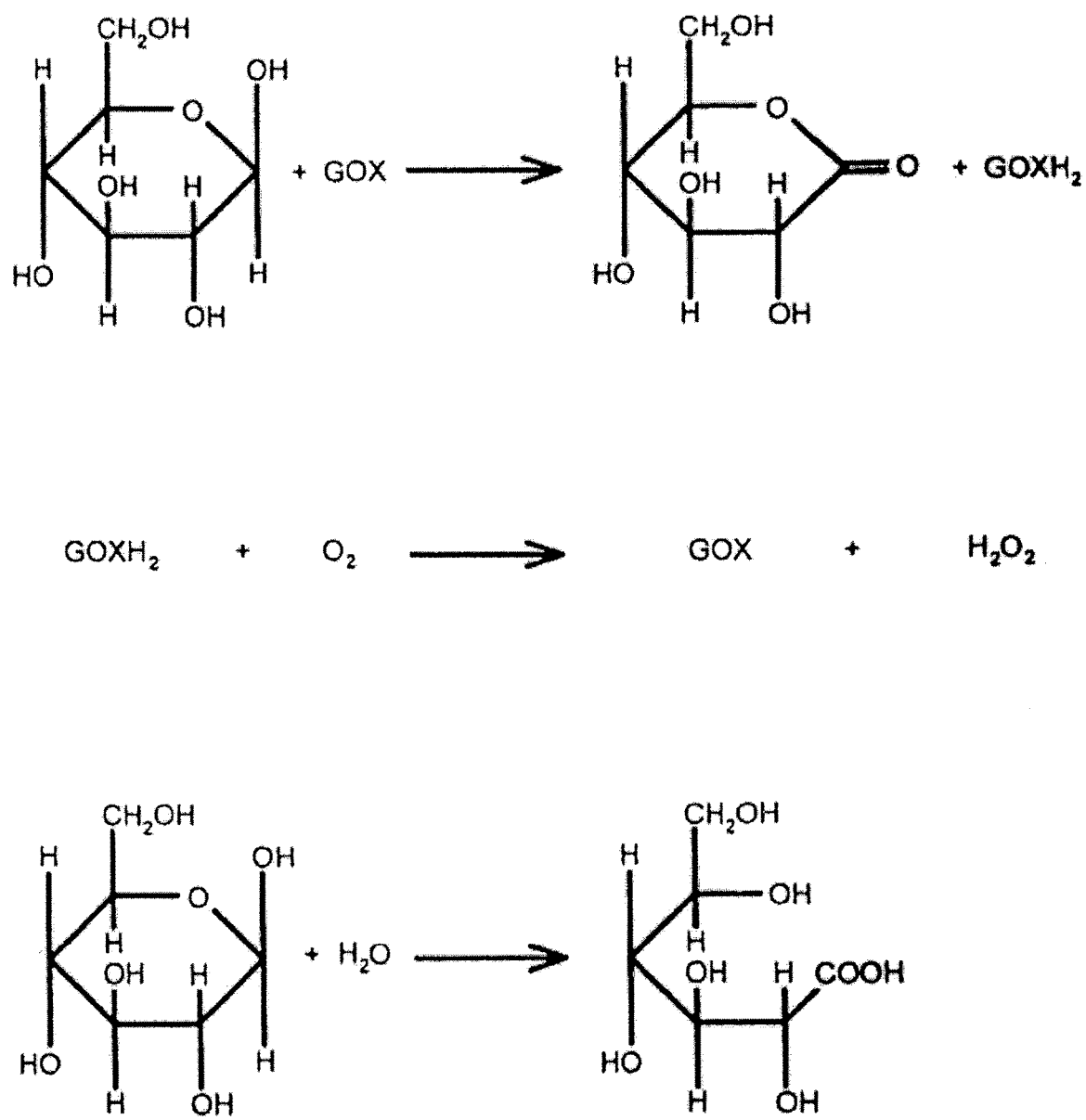
FIG. 1 provides a schematic of the well known reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

Before the present compositions and methods etc. are described, it is to be understood that this invention is not limited to the particular methodology, protocol and reagent described as such may, of course, vary. In addition, those of skill in the art understand that certain sensor and sensor system elements disclosed in one illustrative embodiment can be substituted and/or combined with sensor and sensor system elements disclosed in another illustrative embodiment in order to form yet another embodiment of the invention. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "an oxidoreductase" includes a plurality of such oxidoreductases and equivalents thereof known to those skilled in the art, and so forth. All numbers recited in the specification and associated claims that refer to values that can be numerically characterized with a value other than a whole number (e.g. the concentration of a compound in a solution) are understood to be modified by the term "about".

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The term "oxidoreductase" is used according to its art accepted meaning, i.e. an enzyme that catalyzes the transfer of electrons from one molecule (the reductant, also called the hydrogen or electron donor) to another (the oxidant, also called the hydrogen or electron acceptor). Typical oxidoreductases include glucose oxidase and lactate oxidase. The term "carrier polypeptide" or "carrier protein" is used according to its art accepted meaning of an additive included to maintain the stability of a polypeptide, for example the ability of an oxidoreductase polypeptide to maintain certain qualitative features such as physical and chemical properties (e.g. an ability to oxidize glucose) of a composition comprising a polypeptide for a period of time. A typical carrier protein commonly used in the art is albumin.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

The terms "electrochemically reactive surface" and "electroactive surface" as used herein are broad terms and are used in their ordinary sense, including, without limitation, the surface of an electrode where an electrochemical reaction takes place. In one example, a working electrode measures hydrogen peroxide produced by the enzyme catalyzed reaction of the analyte being detected reacts creating an electric current (for example, detection of glucose analyte utilizing glucose oxidase produces $H_2O_2$ as a by product, $H_2O_2$ reacts with the surface of the working electrode producing two protons ($2H+$), two electrons ($2e-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, the region of a monitoring device responsible for the detection of a particular analyte. In an illustrative embodiment, the sensing region can comprise a non-conductive body, a working electrode, a reference electrode, and a counter electrode passing through and secured within the body forming electrochemically reactive surfaces on the body and an electronic connective means at another location on the body, and a one or more layers covering the electrochemically reactive surface.

The terms "electrical potential" and "potential" as used herein, are broad terms and are used in their ordinary sense, including, without limitation, the electrical potential difference between two points in a circuit which is the cause of the flow of a current. The term "system noise," as used herein, is a broad term and is used in its ordinary sense, including, without limitation, unwanted electronic or diffusion-related noise which can include Gaussian, motion-related, flicker, kinetic, or other white noise, for example.

The terms "interferents" and "interfering species," as used herein, are broad terms and are used in their ordinary sense, including, but not limited to, effects and/or chemical species/compounds that interfere with the measurement of an analyte of interest in a sensor to produce a signal that does not accurately represent the analyte measurement. In one example of an electrochemical sensor, interfering species are compounds with an oxidation potential that overlaps with the analyte to be measured.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte. In some embodiments, the sensor can use an amperometric, coulometric, conductimetric, and/or potentiometric technique for measuring the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391,250, 5,482,473, 5,299,571, 5,568,806, 5,494,562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042, 625, and WO 03/074107, and European Patent Application EP 1153571, the contents of each of which are incorporated herein by reference.

As discussed in detail below, embodiments of the invention disclosed herein provide sensor elements having enhanced material properties and/or architectural configurations and sensor systems (e.g. those comprising a sensor and associated electronic components such as a monitor, a processor and the like) constructed to include such elements. The disclosure further provides methods for making and using such sensors and/or architectural configurations. While some embodiments of the invention pertain to glucose and/or lactate sensors, a variety of the elements disclosed herein (e.g. electrodes and electrode designs) can be adapted for use with any one of the wide variety of sensors known in the art. The analyte sensor elements, architectures and methods for making and using these elements that are disclosed herein can be used to establish a variety of layered sensor structures. Such sensors of the invention exhibit a surprising degree of flexibility and versatility, characteristics which allow a wide variety of sensor configurations to be designed to examine a wide variety of analyte species.

In typical embodiments of the present invention, the transduction of the analyte concentration into a processable signal is by electrochemical means. These transducers may include any of a wide variety of amperometric, potentiometric, or conductimetric base sensors known in the art. Moreover, the micro-fabrication sensor techniques and materials of the instant invention may be applied to other types of transducers (e.g., acoustic wave sensing devices, thermistors, gas-sensing electrodes, field-effect transistors, optical and evanescent field wave guides, and the like) fabricated in a substantially nonplanar, or alternatively, a substantially planar manner. A useful discussion and tabulation of transducers which may be exploited in a biosensor as well as the kinds of analytical applications in which each type of transducer or biosensor, in general, may be utilized, is found in an article by Christopher R. Lowe in Trends in Biotech. 1984, 2(3), 59-65.

Specific aspects of embodiments of the invention are discussed in detail in the following sections.

I. Typical Elements, Configurations and Analyte Sensor Embodiments of the Invention

A. Typical Architectures Found in of Embodiments of the Invention

FIG. 2A illustrates a cross-section of a typical sensor embodiment 100 of a layered sensor as previously described in the art. This sensor embodiment is formed from a plurality of components that are typically in the form of layers of various conductive and non-conductive constituents disposed on each other. The embodiment shown in FIG. 2A includes a base layer 102 made of a metal and/or a ceramic and/or a polymeric substrate to support the sensor 100. A conductive layer 104, typically comprising one or more electrodes, is disposed on and/or combined with the base layer 102. Sensor embodiments with layered electrodes can be found, for example, in U.S. patent Ser. No. 12/184,046, filed Jul. 31, 2008, which is herein incorporated by reference.

In the present invention, as an alternative to the layered electrode scheme discussed above, a wired sensor is provided. A wired sensor configuration can allow for a smaller size of the sensor, which will make for a more unobtrusive sensor as well as a more comfortable sensor. There will be decreased trauma to the patient's skin during insertion as well. The decreased trauma will lead to fewer complications and reduced scarring and physiological reactions due to sensor insertion.

Figure 2B:
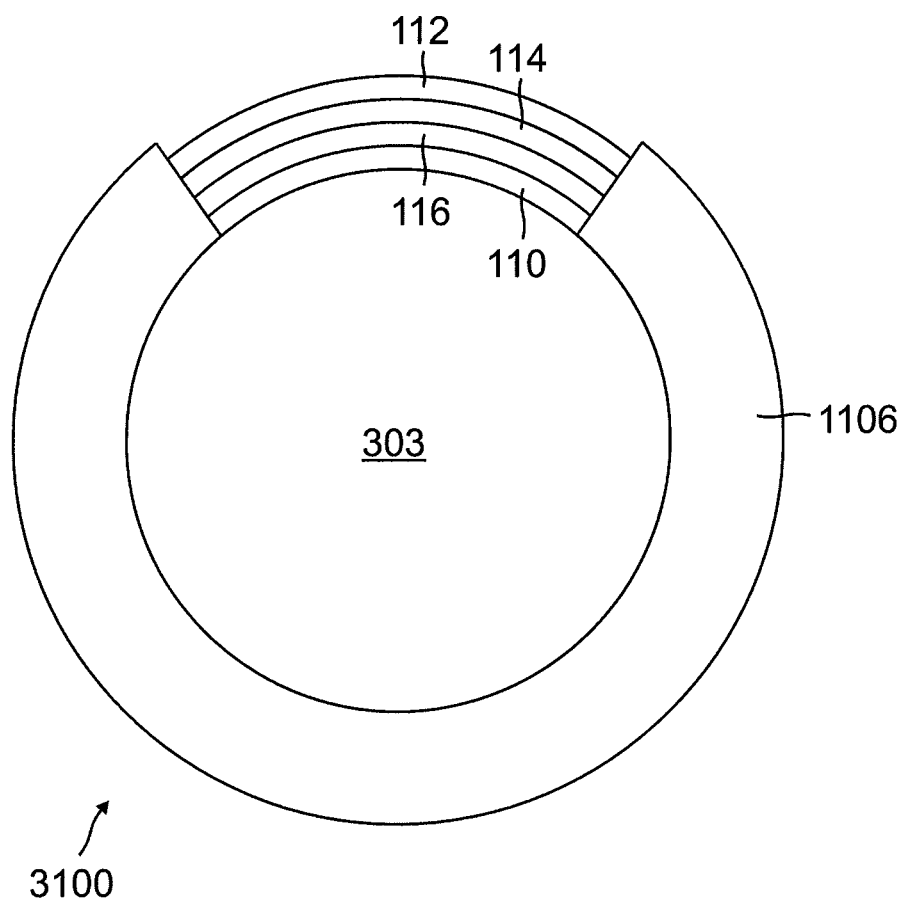
FIG. 2B provides a diagrammatic view of a cross section of the working electrode wire of a wire sensor configuration according to the present invention.

FIG. 2B illustrates a cross-section of one of the wires of a wired sensor in accordance with the present invention. Specifically, FIG. 2B illustrates a cross section of the working electrode portion 303 of the sensor. In the embodiment shown in FIG. 2B, the wire 1104 is substantially covered by an electrically insulating layer 1106. A working electrode area 1108 has been formed in the electrically insulating layer 1106 by creating an aperture or opening that allows access to the wire 1104. The wire at the working electrode area 1108 may be coated with electrode coatings as discussed herein to improve the sensing function of the electrode.

Apertures 1108 can be formed by a number of techniques, including laser ablation, tape masking, chemical milling or etching or photolithographic development or the like, and those described below. The exposed electrode areas secondary processing (e.g. through the apertures), such as additional plating processing, to prepare the surfaces and/or strengthen the conductive regions.

In the configuration shown in FIG. 2B, an analyte sensing layer 1110 (which is typically a sensor chemistry layer, meaning that materials in this layer undergo a chemical reaction to produce a signal that can be sensed by the wire) is disposed on one or more of the exposed electrodes of the wire 1104. Although in FIG. 2B, the chemistry layers are shown only over the wire 1104 at the electrode area/aperture 1108, it is possible that the chemistry layers could be disposed over the entire surface of the wire 1108 such that they are partially covered by the insulating layer 1106.

Typically, the analyte sensing layer 1110 is an enzyme layer. Most typically, the analyte sensing layer 1110 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 1110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode, which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

In embodiments of the invention, the analyte sensing layer 1110 can be applied over portions of the wire or over the entire wire. Typically the analyte sensing layer 1110 is disposed on the working electrode which can be the anode or the cathode. Optionally, the analyte sensing layer 1110 is also disposed on a counter and/or reference electrode. While the analyte sensing layer 1110 can be up to about 1000 microns (μm) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 1110 include brushing the layer onto a substrate (e.g. the reactive surface of a platinum black electrode), as well as spin coating processes, dip and dry processes, low shear spraying processes, ink jet printing processes, silk screen processes and the like. In certain embodiments of the invention, brushing is used to: (1) allow for a precise localization of the layer; and (2) push the layer deep into the architecture of the reactive surface of an electrode (e.g. platinum black produced by an electrodeposition process).

Typically, the analyte sensing layer 1110 is coated and or disposed next to one or more additional layers. Optionally, the one or more additional layers includes a protein layer 1116 disposed upon the analyte sensing layer 1110. Typically, the protein layer 1116 comprises a protein such as human serum albumin, bovine serum albumin or the like. Typically, the protein layer 1116 comprises human serum albumin. In some embodiments of the invention, an additional layer includes an analyte modulating layer 1112 that is disposed above the analyte sensing layer 1110 to regulate analyte contact with the analyte sensing layer 1110. For example, the analyte modulating membrane layer 1112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In typical embodiments of the invention, an adhesion promoter layer 1114 is disposed between the analyte modulating layer 1112 and the analyte sensing layer 1110 as shown in FIG. 2B in order to facilitate their contact and/or adhesion. In a specific embodiment of the invention, an adhesion promoter layer 1114 is disposed between the analyte modulating layer 1112 and the protein layer 1116 as shown in FIG. 2B in order to facilitate their contact and/or adhesion. The adhesion promoter layer 1114 can be made from any one of a wide variety of materials known in the art to facilitate the bonding between such layers. Typically, the adhesion promoter layer 1114 comprises a silane compound. In alternative embodiments, protein or like molecules in the analyte sensing layer 1110 can be sufficiently cross-linked or otherwise prepared to allow the analyte modulating membrane layer 1112 to be disposed in direct contact with the analyte sensing layer 1110 in the absence of an adhesion promoter layer 1114.

In certain embodiments of the invention, a sensor is designed to include additional layers such as an interference rejection layer, discussed below.

Figure 3:
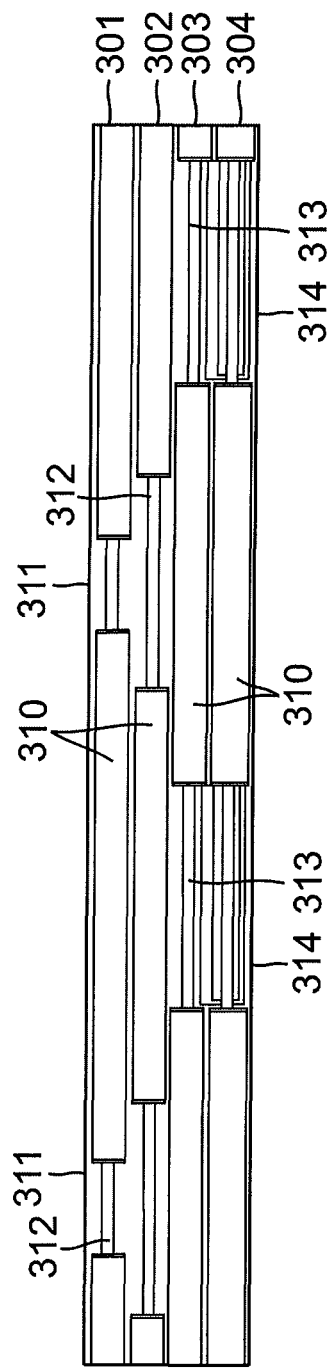
FIG. 3 provides a perspective view of the insertion portion of an embodiment of a wired sensor according the present invention.

An embodiment of the insertion portion of the wire sensor of the present invention is shown further in FIG. 3. As shown in FIG. 3, the sensor may have a number of wires 301-304 that are preferably arranged such that they are running in the same direction. The wires are preferably flexible and electrically conductive wire. Using wire electrodes can improve durability and can be used in methods designed to diminish or overcome problems associated with shaking and bumping of potentially fragile electronic elements that occur when an apparatus flexes as it is used in vivo. In particular, an apparatus implanted in vivo is subjected to a variety of mechanical stresses during a patient's daily routine of activities (e.g., stretching, bending, walking and the like). Such stresses are known in the art to have the ability to damage elements within a device, in particular electrodes, which can be brittle and prone to breakage. Embodiments of the invention are designed to overcome problems by using elements (e.g. a flexible wire electrode) that are less likely to lose optimal function as a result of the mechanical stresses that result from a patient's daily routine of activities.

The embodiment shown in FIG. 3 has four wires, but it is possible to have fewer or more wires. For example, in certain embodiments there are only 2 wires. Each wire would preferably correspond to a sensor. For example, a sensor typically has a working electrode, reference electrode and counter electrode. If each electrode corresponds to a wire, there would be one working electrode wire, one reference electrode wire and one counter electrode wire. Other embodiments may also include a plurality of working and/or counter and/or reference electrodes (and corresponding wires) and/or one or more electrodes that performs multiple functions on a single wire. For example one could have a single wire that functions as both as a working and a counter electrode. In a 2 wire embodiment, for example, there could be a single wire for a reference electrode and a single wire for a working and counter electrode. In addition, there many be 2, 3, 4 or even more combined wires, depending on the number of working electrodes desired for the sensor.

In FIG. 3, four wires are shown, reference electrode wire 301, counter electrode 302, and working electrode wires 303 and 304. The wires could be arranged in a different configuration from that shown. Each wire has a layer coating it made out of an electrically insulating material 310. At least one portion of the electrode insulating material layer 310 on each wire is removed to create an aperture that functions as electrode area 311, 312, 313, and 314. As shown in FIG. 3, there may be two electrode areas on each wire. There may also be just one on each wire or more than two on each wire. It is not necessary that each wire have the same number of electrode areas. For example, the working electrode wire could have three electrode areas while the reference electrode has only two electrode areas.

The electrode areas on each electrode may be of similar size to each other or different sizes. In the example shown in FIG. 3, the working electrode areas 313 and 314 and counter electrode areas 312 are of similar sizes while the reference electrode areas 311 are smaller. Example lengths of electrode areas can be in the range of about 10 to 50 microns. It is possible to have larger lengths, but the smaller areas result in decreased sensor size, which is preferable, among other reasons, for comfort. The electrode areas may all have the same size or may be different sizes.

The wires 301-304 can be extruded material, such as platinum (Pt) or silver (Ag) and/or can be coated with surface enhancing material. Wires that may be used for the working and counter electrodes include platinum, iridium, iridium oxide, and palladium wires. For the reference wire, a silver or silver/silver chloride wire or iridium oxide wire may be used. An electrode coating may be used in addition to the wires. Also, traditional wires of other materials such as gold, platinum, or a platinum/iridium alloy may be used with electrode coatings instead of the wires discussed above. In certain embodiments, the platinum/iridium allow is in a ratio of about 90/10 or 80/20, respectively.

For the electrically insulating material coating the wires, a biocompatible, flexible and electrically insulating material is used. Coatings that provide have these desired properties include polytetrafluoroethylene (PTFE) and PTFE variants like ethylene tetrafluoroethylene (ETFE) and fluorinated ethylene propylene (FEP), polyether block amid (PEBA), polyvinylidene fluoride (PVDF), and thermoplastic elastomers. It is preferable that the coatings reduce pinholes to increase isolation of fluid interaction to the electrode areas, offer biocompatibility, and aid in assembly.

Electrode coatings applied on the wires, especially in the electrode areas, can help provide increased surface areas for reactions with the fluid containing the analyte to be sensed. Electrode coatings for the counter and working electrodes can include platinum black, silver chloride or iridium oxide. The wire base materials may be made out of traditional materials, such as of silver or iridium. Another way to increase surface area is to use a porous wire, such as porous platinum, iridium or platinum coated porous wires. The surface areas of the pores will contact the fluid coming in contact with the electrode area, such that the surface area will become greater than the mere area of coating removed to create the electrode areas.

Iridium oxide coated electrodes have additional advantages. For example, they provide a porous 3-dimensional hydrous environment, which is good for immobilization of enzymes. They also have a catalytic effect on $H_2O_2$ decomposition.

Conducting polymers such as polypyrrole may also be used as electrode coatings. Advantageous conducting polymers have a porous morphology enhancing electrode surface areas, a selectivity of deposition, are good candidates for enzyme immobilization, are conducting and biocompatible.

Surface area modification to increase wire surface area can be made in a number of ways. By increasing the wire surface area, there can be more surface in the same volume of sensor to measure current. Porous metals can be added to the electrodes through electroplating, powder deposition, and sputtering. Porous polymers can be also used as coatings. In addition, mechanical and geometrical modification can be made to the wire metal to create additional surface area by laser micromachining or ion beam etching. The benefit of using mechanical/geometrical modifications is that it is possible to increase surface area by about 2-5 times at the same time as doing laser ablation of the insulating coatings to create the electrode areas. Coatings can be added before insulation is extruded over the wire or may be added after the insulated wire is ablated to create electrode areas.

Further modifications to the surface morphology of the wire electrode areas can be made by electrospray deposition, sonic spray deposition, and the use of supercritical fluid, which may or may not react with the wire metal. It is also possible to change the porosity of polymer coatings, for example by using the processes discussed above.

Figure 8A:
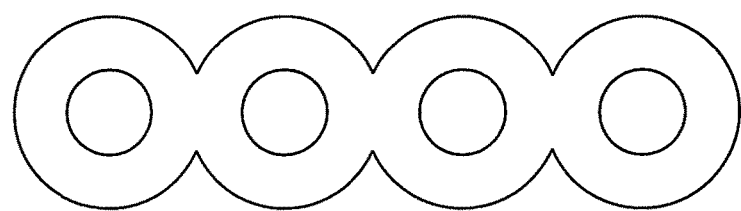
FIG. 8A provides a cross-section view of a round wire flat ribbon configuration of a sensor in accordance with an embodiment of the present invention.
Figure 8B:
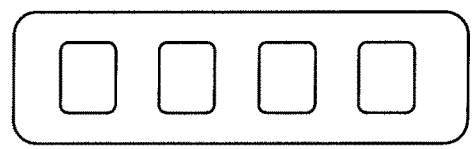
FIG. 8B provides a cross-section view of a flat ribbon wire configuration of a sensor in accordance with an embodiment of the present invention.

The wires may have cross-sections of different shapes. For example, as shown in FIG. 8A, they may be round, which can provide increased surface area. As another example, as shown in FIG. 8B, they may be square or flat wire, which can make it easier to deposit material on locations on the wires. In further embodiments, there may be multiple cross sections within one sensor. For example, one wire could have a round shape and another could have a square shape. Other shapes such as elliptical or oval cross sections are also possible.

Figure 7A:
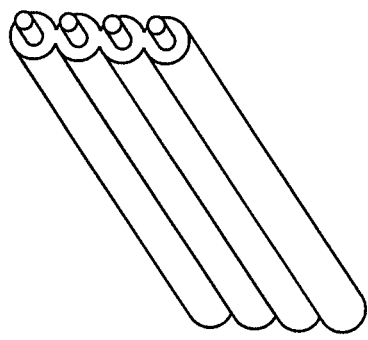
FIG. 7A provides a perspective view of a flat ribbon configuration of a sensor in accordance with an embodiment of the present invention.
Figure 7B:
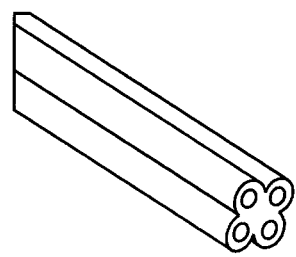
FIG. 7B provides a perspective view of a bundled wire configuration of a sensor in accordance with an embodiment of the present invention.
Figure 7C:
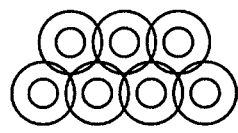
FIG. 7C provides a diagrammatic cross-section view of a stacked wire configuration of a sensor in accordance with an embodiment of the present invention.
Figure 7D:
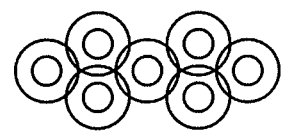
FIG. 7D provides a diagrammatic cross-section view of a stacked wire configuration of a sensor in accordance with an embodiment of the present invention.

It is contemplated that the wires may be extruded in different configurations. As shown in FIG. 7A, one configuration that may be used is a flat ribbon wire configuration. Advantages to using a flat ribbon configuration include that it has a small profile, it makes it easy to deposit material onto the wires, and the configuration can fit easily into a stamped needle. As shown in FIG. 7B, another configuration is a bundled wire configuration. The bundled configuration allows for very efficient packaging and makes it easy for the wires to fit into a round needle. Another example configuration, shown in FIGS. 7C and 7D, is a stacked wire configuration. This allows use of more wires and therefore more conductors with a similar needle profile to that used in the flat ribbon configuration.

It is generally contemplated that the wires will be covered with insulation and then areas of the insulation will be removed to create the electrode areas. The insulation may be removed in any way contemplated by the art that will produce the desired shape and size of electrode areas. These methods include, for example, laser ablation, mechanical removal, and chemical stripping. Advantages of using laser ablation include that it is possible to use the laser to also add texture, and thereby increase surface area, to the electrode area on the wire. No chemicals or solvents are used in laser ablation, which is also an advantage. Additionally, laser ablation allows very precise removal of the insulation, to around +/−5 microns in precision. Alternatively, the insulation can be applied selectively to the wires, to cover all areas except for the electrode areas. By applying the insulation selectively, it is possible to use contamination as an advantage. A material is applied to the wire prior to extrusion that prevents adhesion of the insulation or that will create bubbles that become the exposed electrode areas on the wires.

The use of wires in the sensor allows for improved electrode patterns. The electrode areas may be distributed so that there are multiple electrode openings along the length of one or more of the wires. This ensures sensing even if there is localized biofouling or damage to one of the electrode openings, because there are other electrode openings without the biofouling or damage on the same wire. In addition, it could allow for more uniform plating across a smaller area.

The use of wires also allows for openings on both sides of the sensor. In other words, the wire insulation can be removed around the wire to allow for sensing on both sides to create a larger surface area than allowed in a layered sensor configuration. Alternatively, the wire insulation can be removed on some of the wires on one side and on the other wires on the other side. This means that the counter and reference electrode areas could be on the opposite side from the working electrode areas, allowing separation of the active sensing electrode and improving stability by reducing bioproduct reactions at the working electrode from the counter and reference electrodes.

The chemistry deposited on the working electrode areas, including glucose oxidase (GOx) or other enzyme, is placed on the working electrode areas as in the layered sensor configurations discussed above. In the wired configuration, chemistry deposition is preferably accomplished with a minimal use of solvents. It is advantageous to reduce interaction with solvents that can be harmful to the enzyme. Methods of deposition can include spray coating, for example a pressure based spray or electrospray deposition, supercritical fluid rapid expansion (with or without electrospray deposition), plasma (reactive or otherwise), inkjet or microjet printing of proteins, or microfluidic nozzle fluidic direct interface writing or depositing. Crosslinking may be accomplished, for example, using vapor or plasma. The types of chemistry layers that may be used in the present invention are of the same type that may be used in a layered sensor and are discussed in more detail below.

It is advantageous to use procedures for chemistry deposition that allow for selectivity of the deposition. For example, if the enzyme is only deposited on the working electrode areas, it limits production of peroxide to the area around the electrode that is consuming it. It further allows for an efficient use of materials, minimizing the amount of materials used during fabrication and reducing production costs.

Production of the wire sensors includes singulation of the sensors, separating the individual sensors from a mass production of the sensors. The singulation can be accomplished by laser or mechanical methods. In embodiments of the invention, the tips of the sensor wires are not covered by the electrically insulating covers, for example from singulation where the entire sensors are cut out of a long set of wires that were covered with the insulation together. The uncovered tips, especially those near the electrode areas may then be covered by a tipping layer. Also, tipping can be employed to coat the tips of the wires to prevent exposure to the analyte that would introduce noise. Tipping may be accomplished, for example, using a polyp-xylylene) polymer (Parylene) or other coating as a tipping layer. As discussed below, the sensor at the other end from the electrode areas may have electrical contacts. These could be the uncovered portion of the wires, assuming it exists, at the end opposite from the electrode areas, without having to cut or otherwise define a separate area in the insulating cover. A special tip may also be created that aids in insertion of the sensor into the body.

Figure 10:
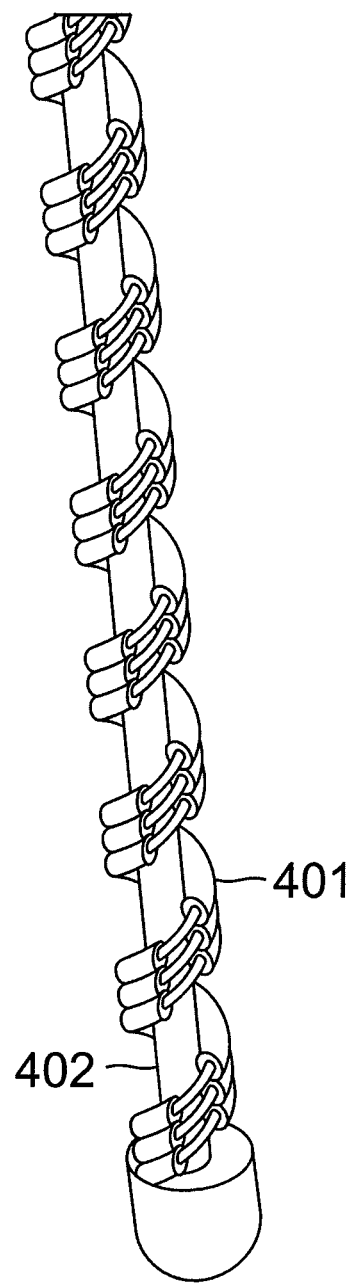
FIG. 10 provides a perspective view of a coiled sensor configuration according to an embodiment of the present invention.

The wire sensor may be configured to be inserted into the body in a linear configuration, such that the wires line up next to each other in a straight line that enters into the body at the same angle as the needle carrying the sensor. Alternatively, a coiled sensor configuration may be used. FIG. 10 shows a coiled design where the wires 401 coil around a central core 402. The central core 402 is then what preferably enters the body at the same angle as the needle carrying the sensor. The use of a coiled sensor is possible with a small electrode size. The diameter of the entire coil, including the core and wires, is preferably less than about 0.013 inches to minimize the size of the implant. The coiled configuration offers the advantage of increasing the surface area for the same depth of sensor by about 2-3 times over the linear sensor configuration. The core material may be made out of any material that is biocompatible and allows some flexibility but sufficient structure for the coil. Examples of core material include a coated polymer, hydrogels, or a shape memory alloy (e.g. a nickel titanium alloy such as NITINOL). The advantage of using a shape memory alloy is that the sensor can be more stiff during the implant and then soften during wear. It can also help direct sensor placement to an optimal location. The wire can be coiled before or after the chemistry is deposited on the electrode areas.

The needle design of the insertion tool used to insert the sensor may be similar to that used in a layered sensor system. Additional design elements may be used that would benefit the wire sensor configuration. For example, in a ribbon or stacked cable configuration, a stamped sensor needle may be used. A stamped sensor needle can be thin and provides good protection of the sensor during insertion. Low insertion force is required due to the sensor being enclosed in the needle. The stamped sensor easily fits a ribbon or stacked sensor profile. As with the coiled sensor discussed above, the addition of shape memory properties can be included in the stamped sensor needle to direct placement of the sensor in the body. Optimal locations, for example, include locations chosen to reduce the likelihood of a sensor being removed from the body.

Figure 11A:
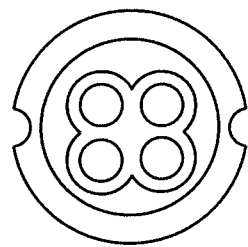
FIG. 11A provides a cross-section view of a bundled wire configuration sensor with a split needle in accordance with an embodiment of the present invention.
Figure 11B:
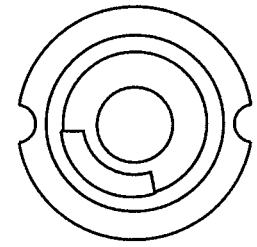
FIG. 11B provides a cross-section view of a coiled cable configuration sensor with a split needle in accordance with an embodiment of the present invention.
Figure 11C:
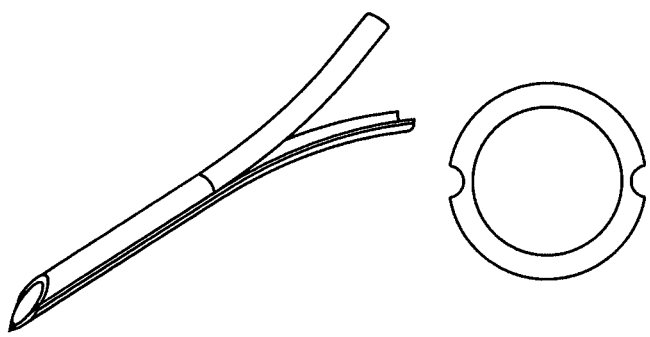
FIG. 11C provides a perspective view of a split needle in accordance with an embodiment of the present invention.

In a bundled or coiled cable configuration, although a stamped needle could be used depending on the size of the sensor and needle, a split needle could provide additional benefits. As shown in FIGS. 11A-C, the split needle 501 is a full, round needle, which contains the sensor inside. FIG. 11A shows a bundled wire configured sensor and FIG. 11B shows a coiled cable configured sensor. FIG. 11C shows a side view of the split needle itself. In further configurations, the needle could be oval or another shape that contours around the sensor. The split needle may "unzip" as it is pulled off, leaving the sensor behind. It may be made of a stiff plastic to aid in ease of manufacturing, allowing for extrusion over the sensor. Because the sensor would be fully enclosed, the needle would provide great protection for delicate sensors and would require a low insertion force, because the delicate sensor would be enclosed in the stiff needle.

In further embodiments, the sensor can employ a needleless design. In such a design, the tip of the sensor may be formed to aid in insertion, for example in a pointed shape. The properties of the core in the coiled configuration or in one or more of the extruded wires in the more linear configurations such as the ribbon cable configuration could be formulated to aid in insertion. For example, they could have shape memory properties that allow for a more stiff sensor out of the body that becomes more flexible when inside the body. Other heat softening materials may also be used, to create a comfortable sensor that is also easy to insert.

B. Typical Analyte Sensor Constituents Used in Embodiments of the Invention

The following disclosure provides examples of typical elements/constituents used in sensor embodiments of the invention. While these elements can be described as discreet units, those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Conductive Wire

The electrochemical sensors of the invention typically include one or more conductive wires as the main structure for each electrode. The term "conductive wire" is used herein according to art accepted terminology and refers to electrically conductive wires which are capable of measuring a detectable signal and conducting this to a detection apparatus. An illustrative example of this is a conductive wire that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 1110 or a reaction product of this interaction (e.g. hydrogen peroxide). Illustrative examples of such elements include electrodes on wires which are capable of producing variable detectable signals in the presence of variable concentrations of molecules such as hydrogen peroxide or oxygen. Electrode areas, or electrodes, are formed on the wires by removing a portion of the electrically insulating layer that has been extruded over the wire. Alternatively, a method could be used to create the electrode areas during extrusion of the electrically insulating layer, such that the electrically insulating layer does not adhere to the wire at the desired area for the electrode.

Typically one of these electrodes on the conductive wire (s) is working electrode. As discussed above, the working electrode wire may be platinum, iridium, iridium oxide and/or palladium and may be extruded as such or an extruded generic base wire (e.g., gold, platinum or platinum/iridium alloy) with a coating on the electrode area(s) or the entire wire. Typically, only a portion of the surface of the metallic or carbon conductor is in electrolytic contact with the analyte-containing solution. This portion is called the working surface of the electrode or electrode area. The remaining surface of the wire is typically isolated from the solution by an electrically insulating layer 1106, which is generally extruded over the wires. Examples of useful materials for generating this include polymers such as polyimides, polytetrafluoroethylene, polyhexafluoropropylene and silicones such as polysiloxanes. A biocompatible, flexible and electrically insulating material is used. Coatings that provide have these desired properties include polytetrafluoroethylene (PTFE) and PTFE variants like ethylene tetrafluoroethylene (ETFE) and fluorinated ethylene propylene (FEP), polyether block amid (PEBA), polyurethane, silicone, and their co-block polymers, polyvinylidene fluoride (PVDF), and thermoplastic elastomers. It is preferable that the coatings reduce pinholes to increase isolation of fluid interaction to the electrode areas, offer biocompatibility, and aid in assembly.

In addition to the working electrode, the analyte sensors of the invention typically include a reference electrode or a combined reference and counter electrode (also termed a quasi-reference electrode or a counter/reference electrode) on a separate wire. If the sensor does not have a counter/reference electrode then it may include a separate counter electrode wire, which may be made from the same or different materials as the working electrode wire. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected, for example by being on the same wire, or they may be kept separate and on separate wires.

Typically for in vivo use, embodiments of the present invention are implanted subcutaneously in the skin of a mammal for direct contact with the body fluids of the mammal, such as blood. Alternatively the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal.

Interference Rejection Constituent

The electrochemical sensors of the invention optionally include an interference rejection constituent disposed between the surface of one or more of the wire's electrode areas and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic polyurethanes, cellulose acetate (including cellulose acetate incorporating agents such as poly(ethylene glycol), polyethersulfones, polytetrafluoroethylenes, the perfluoronated ionomer Nafion™, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference. Other interference rejection constituents include for example those observed to limit the movement of compounds based upon a molecular weight range, for example cellulose acetate as disclosed for example in U.S. Pat. No. 5,755,939, the contents of which are incorporated by reference.

Exemplary interference rejection constituents useful with embodiments of the invention are disclosed in U.S. patent application Ser. No. 12/572,087, the contents of which are incorporated herein by reference. One example of an interference rejection membrane (IRM) useful in embodiments of the invention comprises a polymeric composition comprising methacrylate polymers having a molecular weight between 100 and 1000 kilodaltons, wherein the methacrylate polymers are crosslinked by a hydrophilic crosslinking agent such as an organofunctional dipodal alkoxysilane. Another IRM embodiment of the invention is a polymeric composition comprising primary amine polymers having a molecular weight between 4,000 Daltons and 500 kilodaltons, wherein the primary amine polymers are crosslinked by a hydrophilic crosslinking agent such as glutaraldehyde. Typically these crosslinked polymeric IRM compositions coat sputtered platinum composition. In an illustrative embodiment, the platinum composition comprises an electrode; and the crosslinked polymeric composition is coated on the electrode in a layer between 0.1 μm and 1.0 μm thick. A related embodiment of the invention is a composition comprising an electrode (e.g. a sputtered platinum electrode used in an amperometric sensor) having an electroactive surface coated with and in direct contact with a layer of crosslinked methacrylate polymers or crosslinked primary amine polymers. In certain embodiments of the invention, the IRM is designed to function (i.e. inhibit the diffusion of an interferent) where the molecular weight of the interferent is at least 140 Daltons. Typically, the IRM inhibits the diffusion of acetaminophen, ascorbic acid and/or uric acid there through to the electroactive surface of an electrode within an analyte sensor.

Analyte Sensing Constituent

The electrochemical sensors of the invention include an analyte sensing constituent disposed on the electrodes of the sensor (see, e.g. element 1110 in FIG. 2B). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive wires. In this regard the analyte sensing constituent and the electrodes of the conductive wires work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes/electrode areas of the sensor. In this context, the analyte sensing constituent may coat the electrodes/electrode areas to an equivalent degree. Alternatively the analyte sensing constituent may coat different electrodes/electrode areas to different degrees, with for example the coated surface of the working electrode area being larger than the coated surface of the counter and/or reference electrode area.

Typical sensor embodiments of this element of the invention utilize an enzyme (e.g. glucose oxidase (GOx)) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide according to the reaction shown in FIG. 1, wherein the hydrogen peroxide so generated is anodically detected at the working electrode in the working conductive wire.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde. Other suitable cross-linkers also may be used, as will be evident to those skilled in the art.

The GOx and/or carrier protein concentration may vary for different embodiments of the invention. For example, the GOx concentration may be within the range of approximately 50 mg/ml (approximately 10,000 U/ml) to approximately 700 mg/ml (approximately 150,000 U/ml). Typically the GOx concentration is about 115 mg/ml (approximately 22,000 U/ml). In such embodiments, the HSA concentration may vary between about 0.5%-30% (w/v), depending on the GOx concentration. Typically the HSA concentration is about 1-10% w/v, and most typically is about 5% w/v. In alternative embodiments of the invention, collagen or BSA or other structural proteins used in these contexts can be used instead of or in addition to HSA. Although GOx is discussed as an illustrative enzyme in the analyte sensing constituent, other proteins and/or enzymes may also be used or may be used in place of GOx, including, but not limited to glucose dehydrogenase or hexokinase, hexose oxidase, lactate oxidase, and the like. Other proteins and/or enzymes may also be used, as will be evident to those skilled in the art. Moreover, although HSA is employed in the example embodiment, other structural proteins, such as BSA, collagens or the like, could be used instead of or in addition to HSA.

As noted above, in some embodiments of the invention, the analyte sensing constituent includes a composition (e.g. glucose oxidase) capable of producing a signal (e.g. a change in oxygen and/or hydrogen peroxide concentrations) that can be sensed by the electrode areas of the conductive wires (e.g. electrodes which sense changes in oxygen and/or hydrogen peroxide concentrations). However, other useful analyte sensing constituents can be formed from any composition that is capable of producing a detectable signal that can be sensed by the electrode areas of the electrically conductive wires after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; (Jan. 7, 1991) the entire contents of which are incorporated herein by reference.

Other useful analyte sensing constituents can be formed to include antibodies whose interaction with a target analyte is capable of producing a detectable signal that can be sensed by the electrodes of the electrically conductive wires after interacting with the target analyte whose presence is to be detected. For example U.S. Pat. No. 5,427,912 (which is incorporated herein by reference) describes an antibody-based apparatus for electrochemically determining the concentration of an analyte in a sample. In this device, a mixture is formed which includes the sample to be tested, an enzyme-acceptor polypeptide, an enzyme-donor polypeptide linked to an analyte analog (enzyme-donor polypeptide conjugate), a labeled substrate, and an antibody specific for the analyte to be measured. The analyte and the enzyme-donor polypeptide conjugate competitively bind to the antibody. When the enzyme-donor polypeptide conjugate is not bound to antibody, it will spontaneously combine with the enzyme acceptor polypeptide to form an active enzyme complex. The active enzyme then hydrolyzes the labeled substrate, resulting in the generation of an electroactive label, which can then be oxidized at the surface of an electrode. A current resulting from the oxidation of the electroactive compound can be measured and correlated to the concentration of the analyte in the sample. U.S. Pat. No. 5,149,630 (which is incorporated herein by reference) describes an electrochemical specific binding assay of a ligand (e.g., antigen, hapten or antibody) wherein at least one of the components is enzyme-labelled, and which includes the step of determining the extent to which the transfer of electrons between the enzyme substrate and an electrode, associated with the substrate reaction, is perturbed by complex formation or by displacement of any ligand complex relative to unbound enzyme-labelled component. U.S. Pat. No. 6,410,251 (which is incorporated herein by reference) describes an apparatus and method for detecting or assaying one constituting member in a specific binding pair; for example, the antigen in an antigen/antibody pair, by utilizing specific binding such as binding between an antigen and an antibody, together with redox reaction for detecting a label, wherein an oxygen micro-electrode with a sensing surface area is used. In addition, U.S. Pat. No. 4,402,819 (which is incorporated herein by reference) describes an antibody-selective potentiometric electrode for the quantitative determination of antibodies (as the analyte) in dilute liquid serum samples employing an insoluble membrane incorporating an antigen having bonded thereto an ion carrier effecting the permeability of preselected cations therein, which permeability is a function of specific antibody concentrations in analysis, and the corresponding method of analysis. For related disclosures, see also U.S. Pat. Nos. 6,703,210, 5,981,203, 5,705,399 and 4,894,253, the contents of which are incorporated herein by reference.

In addition to enzymes and antibodies, other exemplary materials for use in the analyte sensing constituents of the sensors disclosed herein include polymers that bind specific types of cells or cell components (e.g. polypeptides, carbohydrates and the like); single-strand DNA; antigens and the like. The detectable signal can be, for example, an optically detectable change, such as a color change or a visible accumulation of the desired analyte (e.g., cells). Sensing elements can also be formed from materials that are essentially non-reactive (i.e., controls). The foregoing alternative sensor elements are beneficially included, for example, in sensors for use in cell-sorting assays and assays for the presence of pathogenic organisms, such as viruses (HIV, hepatitis-C, etc.), bacteria, protozoa and the like.

Also contemplated are analyte sensors that measure an analyte that is present in the external environment and that can in itself produce a measurable change in current at an electrode. In sensors measuring such analytes, the analyte sensing constituent can be optional.

Protein Constituent

The electrochemical sensors of the invention optionally include a protein constituent disposed between the analyte sensing constituent and the analyte modulating constituent (see, e.g. element 1116 in FIG. 2B). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 1114 in FIG. 2B). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula R'Si(OR)$_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase (GOX) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such a the analyte sensing constituent and/or the protein constituent and or a siloxane moiety present in a compound disposed in a proximal layer such as the analyte modulating layer.

Analyte Modulating Constituent

The electrochemical sensors of the invention include an analyte modulating constituent disposed on the sensor (see, e.g. element 112 in FIG. 2). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. O$_2$).

With respect to glucose sensors, in known enzyme electrodes, glucose and oxygen from blood, as well as some interferents, such as ascorbic acid and uric acid, diffuse through a primary membrane of the sensor. As the glucose, oxygen and interferents reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771, 868 and 5,391,250, the disclosures of each being incorporated herein by reference. The hydrogels described therein are particularly useful with a variety of implantable devices for which it is advantageous to provide a surrounding water constituent. In some embodiments of the invention, the analyte modulating composition includes PDMS. In certain embodiments of the invention, the analyte modulating constituent includes an agent selected for its ability to crosslink a siloxane moiety present in a proximal constituent. In closely related embodiments of the invention, the adhesion promoting constituent includes an agent selected for its ability to crosslink an amine or carboxyl moiety of a protein present in a proximal constituent.

Exemplary analyte modulating layers useful with embodiments of the invention are disclosed in U.S. patent application Ser. No. 12/643,790, the contents of which are incorporated herein by reference. In some embodiments of the invention, the analyte modulating layer is formed to comprise a blended mixture of a linear polyurethane/polyurea polymer and a branched acrylate polymer blended together at a ratio of between 1:1 and 1:20 by weight %, with the polyurethane/polyurea polymer being formed from a mixture comprising a diisocyanate; a hydrophilic polymer comprising a hydrophilic diol or hydrophilic diamine; and a siloxane having an amino, hydroxyl or carboxylic acid functional group at a terminus; and the branched acrylate polymer formed from a mixture comprising a butyl, propyl, ethyl or methyl-acrylate; an amino-acrylate; a siloxane-acrylate; and a poly(ethylene oxide)-acrylate. Typically the analyte modulating layer is formed to exhibit a permeability to glucose that changes less than 2% per degree centigrade over a temperature range of 22 to 40 degrees centigrade.

Electrically Insulating Cover

The electrochemical sensors of the invention include one or more cover constituents which are typically electrically insulating protective materials that are extruded over the conductive wires (see, e.g. element 1106 in FIG. 2B). For the electrically insulating material coating the wires, a biocompatible, flexible and electrically insulating material is used. Coatings that have these desired properties include polytetrafluoroethylene (PTFE) and PTFE variants like ethylene tetrafluoroethylene (ETFE) and fluorinated ethylene propylene (FEP), polyether block amid (PEBA), polyvinylidene fluoride (PVDF), and thermoplastic elastomers. It is preferable that the coatings reduce pinholes to increase isolation of fluid interaction to the electrode areas, offer biocompatibility, and aid in assembly Acceptable electrically insulating material coatings can include, but are not limited to, non-toxic biocompatible polymers such as silicone compounds, polyimides, biocompatible solder masks, epoxy acrylate copolymers, or the like. Specifically, coatings that provide the desired properties include polytetrafluoroethylene (PTFE) and PTFE variants like ethylene tetrafluoroethylene (ETFE) and fluorinated ethylene propylene (FEP), polyether block amid (PEBA), polyvinylidene fluoride (PVDF), and thermoplastic elastomers. It is preferable that the coatings reduce pinholes to increase isolation of fluid interaction to the electrode areas, offer biocompatibility, and aid in assembly. Further, these coatings can be photo-imageable to facilitate photolithographic forming of apertures through to the conductive wire.

C. Typical Analyte Sensor System Embodiments of the Invention

Embodiments of the sensor elements and sensors can be operatively coupled to a variety of other systems elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Embodiments of the invention include devices which display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide providing real-time sensor glucose (SG) values. Values/graphs are displayed on a monitor of the pump receiver so that a user can self monitor blood glucose and deliver insulin using their own insulin pump. Typically an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values include a plurality of measurements of blood glucose.

Figure 4:
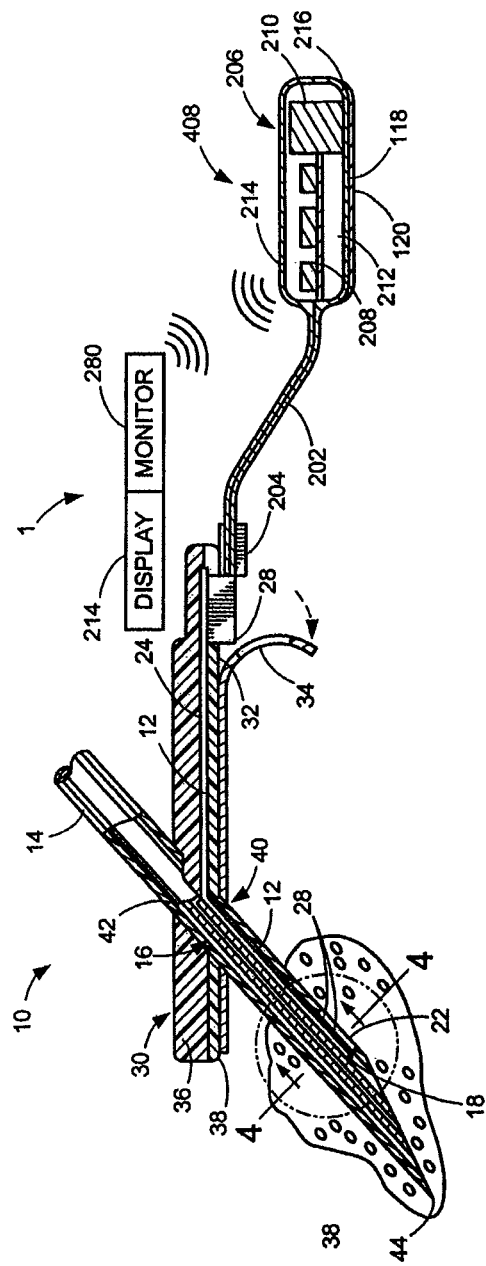
FIG. 4 provides a perspective view illustrating one embodiment of a subcutaneous sensor insertion set, a telemetered characteristic monitor transmitter device, and a data receiving device embodying features of the invention.

FIG. 3 provides a perspective view of one generalized embodiment of subcutaneous sensor insertion system and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 4 provides a perspective view of a telemetered characteristic monitor system 1, including a subcutaneous sensor set 10 provided for subcutaneous placement of an active portion of a sensor 12, or the like, at a selected site in the body of a user.

The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20, which are on wires according to the present invention, to the user's bodily fluids through a window 22 formed in the cannula 16. The sensing portion 18 may be a portion of the wires in the sensor or separate wires that connect to the rest of the sensor. The sensing portion is joined to a connection portion 24 that terminates in conductive contacts, or the like, which are also exposed through one of the insulative layers. In other words, each of the plurality of sensor wires is exposed from the electrically insulating cover at a portion defining a contact in electrical communication with the electrode area on that wire. Preferably, the electrode areas are substantially near or at a first end of the plurality of wires and the contacts are substantially near or at the other, second end of the plurality of wires. In one embodiment, the sensing portion, connection portion and conductive contacts are all part of the same wires. For example, if there is one working electrode wire, one reference electrode wire, and one counter electrode wire in the sensor, the three wires, joined together to form the sensor, would run from the inserted end, which would include the sensing portion, through the connection portion to the other end that will connect to the monitor or transmitter (e.g., contacts). The connection portion 24 and the contacts are generally adapted for a direct wired electrical connection to a suitable monitor 200 coupled to a display 314 for monitoring a user's condition in response to signals derived from the sensor electrodes 20. The connection portion 24 may be conveniently connected electrically to the monitor 200 or a characteristic monitor transmitter 400 by a connector block 28 (or the like) as shown and described in U.S. Pat. No. 5,482,473, entitled FLEX CIRCUIT CONNECTOR, which is incorporated by reference.

As shown in FIG. 4, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and further through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 400 is coupled to a sensor set 10 by a cable 202 through a connector 204 that is electrically coupled to the connector block 28 of the connector portion 24 of the sensor set 10.

In the embodiment shown in FIG. 4, the telemetered characteristic monitor 400 includes a housing 206 that supports a printed circuit board 208, batteries 210, antenna 212, and the cable 202 with the connector 204. In some embodiments, the housing 206 is formed from an upper case 214 and a lower case 216 that are sealed with an ultrasonic weld to form a waterproof (or resistant) seal to permit cleaning by immersion (or swabbing) with water, cleaners, alcohol or the like. In some embodiments, the upper and lower case 214 and 216 are formed from a medical grade plastic. However, in alternative embodiments, the upper case 214 and lower case 216 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 216 may have an underside surface coated with a suitable pressure sensitive adhesive layer 118, with a peel-off paper strip 120 normally provided to cover and protect the adhesive layer 118, until the sensor set telemetered characteristic monitor transmitter 400 is ready for use.

In the illustrative embodiment shown in FIG. 4, the subcutaneous sensor set 10 facilitates accurate placement of an electrochemical sensor 12, wired or thin film, of the type used for monitoring specific blood parameters representative of a user's condition. The sensor 12 monitors glucose levels in the body, and may be used in conjunction with automated or semi-automated medication infusion pumps of the external or implantable type as described in U.S. Pat. No. 4,562,751; 4,678,408; 4,685,903 or 4,573,994, to control delivery of insulin to a diabetic patient.

In the illustrative embodiment shown in FIG. 4, the sensor electrodes 10 may be used in a variety of sensing applications and may be configured in a variety of ways. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 4, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 202 through a connector that is electrically coupled to the connector block 28 of the connection portion 24. In an alternative embodiment, the cable may be omitted. In this embodiment of the invention, the monitor 200 may include an appropriate connector for direct connection to the connection portion 204 of the sensor set 10. The sensor set 10 may be modified to have the connector portion 204 positioned at a different location, e.g., on top of the sensor set to facilitate placement of the monitor 200 over the sensor set.

Although the sensor set shown in FIG. 4 is depicted as having the sensor angled such that it is at an angle much less than 90 degrees from the mounting base, in further embodiments, the sensor may be at an angle of substantially 90 degrees from the mounting base of the sensor set. In FIGS. 5A-6C, a sensor set configuration is shown where the sensor leads directly down from the mounting base 30 out of an opening 70 such that it may enter the body of a patient at an angle of substantially 90 degrees.

Figure 5A:
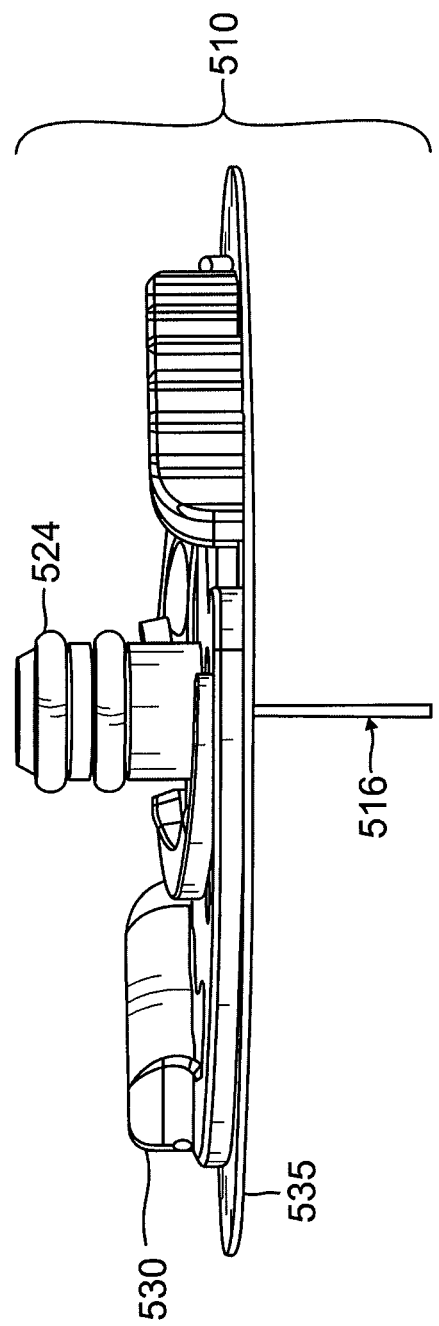
FIG. 5A provides a perspective view illustrating a subcutaneous sensor set in accordance with an embodiment of the present invention.

FIG. 5A depicts a sensor set 510 according to an embodiment of the present invention. It may include any of the components discussed above and may be connected to sensor electronics and a transmitter and/or monitor also as discussed above. FIG. 5A shows the sensor set adapted to connect to a transmitter or other hub through a connector portion 524. The sensor set could connect to a hub that leads directly to a monitor or the hub could include the monitor itself. The sensor set includes a base 530 and may also include a patch 535 that can adhere to the skin of a patient. The patch 535 may have an adhesive on it and a removable paper or other thin layer that may be removed to expose the adhesive before the cannula 516 is inserted into the patient's skin. The sensor (not shown) is within the cannula 516. In further embodiments, the sensor may extend out of the cannula 516 such that a portion of the sensor sits inside the patient's body without a cannula surrounding it. In still further embodiments, the sensor may be inserted without a cannula.

Figure 5B:
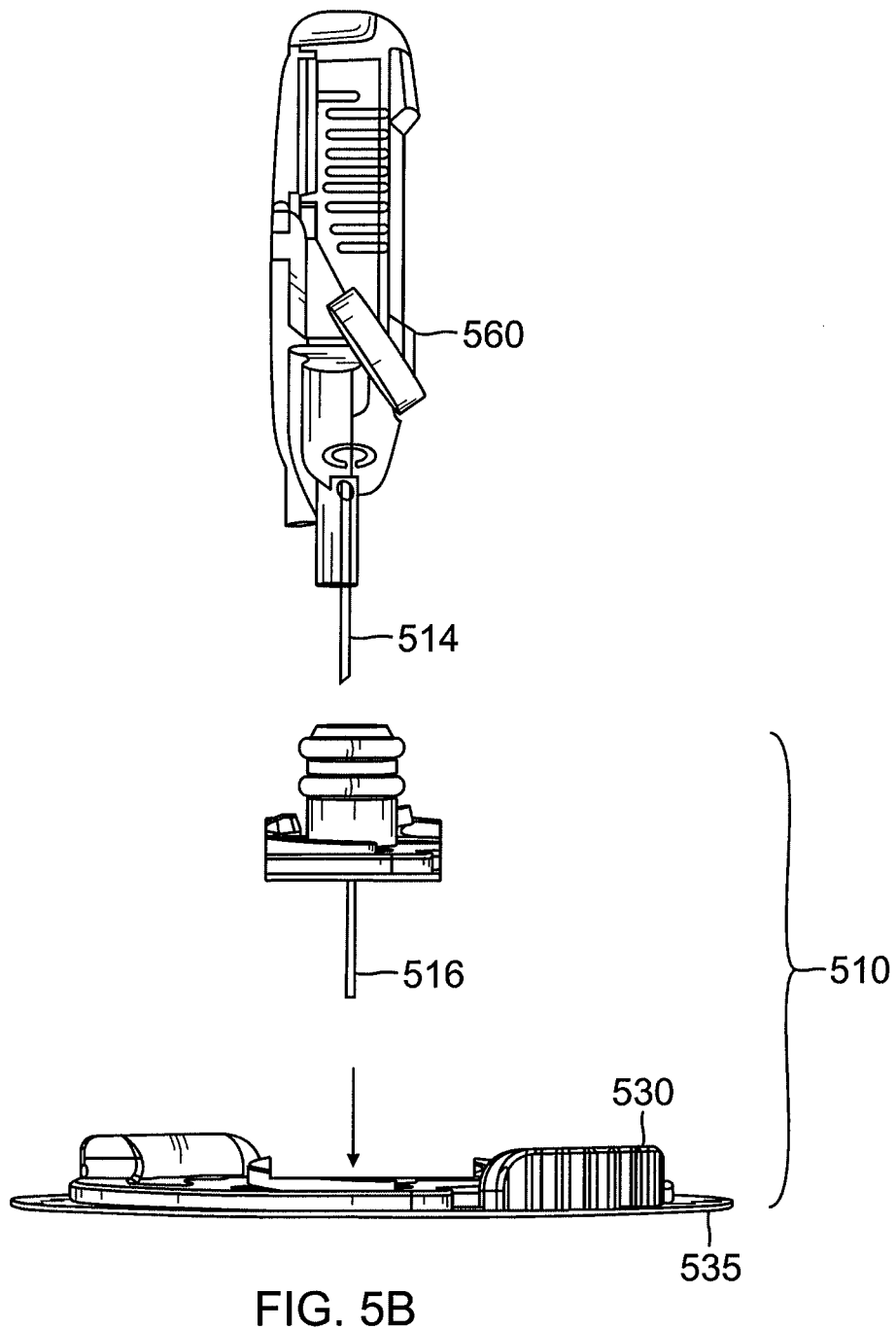
FIG. 5B provides a perspective view illustrating an expanded view of the embodiment shown in FIG. 5A and an insertion tool in accordance with an embodiment of the present invention.

FIG. 5B shows the sensor set 510 with an insertion tool 560. In the embodiment shown in FIG. 5B, the connector portion 524 has been shown as separate from the base 530. This is generally for illustrative purposes. It is possible that the sensor set 510 could be any number of distinct pieces or that it is one combined piece that is not meant to be connected or disconnected after manufacture. The insertion tool 560 on the other hand is intended to be a separate piece from the sensor set 510. It may be packaged together with the sensor set or separate from the sensor set. The insertion tool has a needle 514 that is inserted into the cannula 516 to assist in placement of the cannula 516 in the body. The needle 516 may extend out of the insertion tool 560. The needle also may be adapted such that it is initially held within the insertion tool and hidden from the user, only extending into the cannula when the user connects the insertion tool to the sensor set in order to insert it into the body. The needle may then retract back into the insertion tool when the sensor set is separated from the insertion tool, keeping the needle hidden from the user. Insertion tools that may be used in conjunction with this invention are disclosed, for example, in U.S. patent application Ser. No. 11/645,435, filed Dec. 26, 2006, and U.S. patent application Ser. No. 11/211,095, filed Aug. 23, 2005, each of which is incorporated herein by reference. Other examples of insertion tools are described in U.S. Patent Application Publication No. 2002/0022855 (assigned to the assignee of the present invention), which is incorporated herein by reference. Other examples of needle/cannula insertion tools that may be used (or modified for use) to insert a needle and/or cannula, are described in, for example U.S. patent application Ser. No. 10/389,132 filed Mar. 14, 2003 and/or U.S. patent application Ser. No. 10/314,653 filed Dec. 9, 2002, both of which are incorporated herein by reference in their entirety. In further embodiments, a simple needle or simplified insertion tool, such as discussed above, could be used to insert the sensor set. In still further embodiments, the sensor itself is stiff enough that a needle is not necessary, for example by using a memory metal that is stiff outside the body and softens in the body.

Figure 6A:
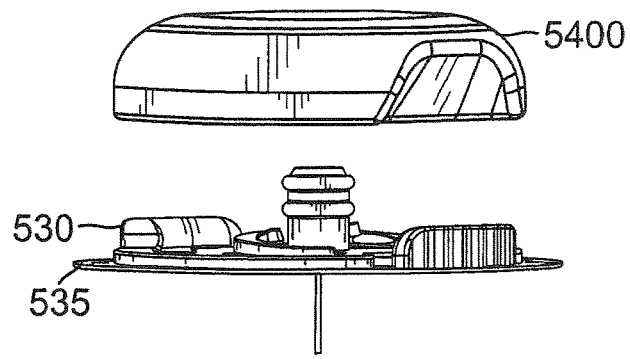
FIG. 6A provides a perspective, expanded view illustrating an embodiment of a sensor transmitter and sensor set according to an embodiment of the present invention.
Figure 6B:
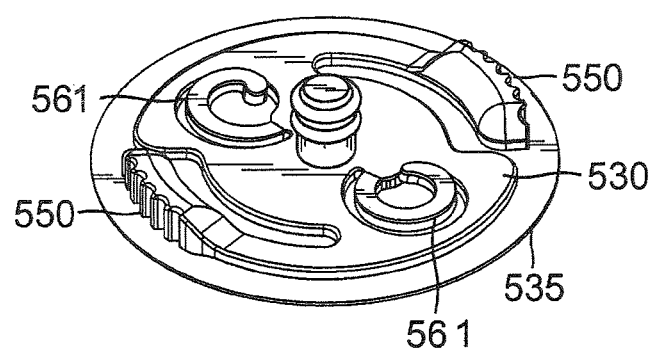
FIG. 6B provides another perspective view of the embodiment shown in FIG. 6A, without the sensor transmitter.

FIG. 6B shows a different view of a sensor set in accordance with an embodiment of the present invention. FIGS. 6A and 6B show a transmitter 5400 and sensor set in accordance with an embodiment of the present invention. The transmitter 5400 is adapted to electrically connect to the analyte sensor when the mounting base 30 and transmitter are connected. As shown in FIG. 6B, the base 530 may have pinch levers 550 that are adapted to release the transmitter 5400 when pinched. The pinch levers 550 may snap into the transmitter 5400 when the base is connected to the transmitter and then release from the transmitter when pinched. The disconnection may be further accomplished, for example, through the use of ejection springs 561 that push the transmitter 5400 away from the base when the pinch levers 550. The transmitter 5400 contains electronics that allow signals from the sensor to be transmitted to a monitor. The transmitter 5400 may also contain electronics to convert the signals to readable data, to store signals and/or data, to display data, and other desirable functions of a transmitter or monitor, which are discussed above and in U.S. Pat. Nos. 6,558,351, 7,344,500, and 7,278,983, which are herein incorporated by reference.

Figure 6C:
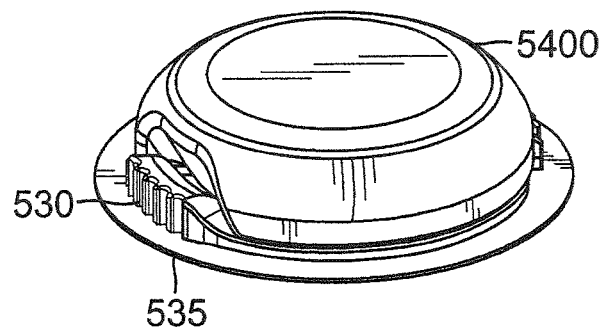
FIG. 6C provides a non-expanded view of the embodiment shown in FIGS. 6A and 6B.

By using the structure shown in FIGS. 6A-C, it is possible to minimize the space the sensor set and transmitter take up on the body. It is also possible to get better alignment of the base to the transmitter over other side to side configurations.

In the manufacture of a sensor set in accordance with the present invention, the sensor set may be manufactured from the top down to eliminate the need to flip the sensor base around. In one embodiment, the sensor electronics are the last component to be assembled into the sensor set. It is beneficial to limit the number of components being assembled to reduce strains, potential flaws and cost. Adhesive can be used to bond the patch to the base and seal other junctions, like the bore for the sensor and the cap over the sensor. It is possible to use glue-less processes to join these junctions as well.

Figure 12:
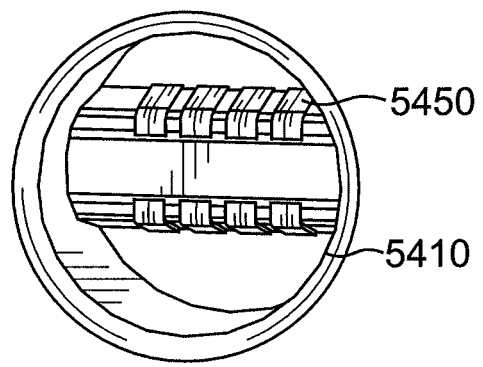
FIG. 12 provides a perspective view of transmitter pins in accordance with an embodiment of the present invention.

The transmitter may have pins to connect to the contacts of the sensor set at the connector portion. The pins can electrically connect the transmitter to the analyte sensor when the connecting portion of the mounting base is inserted in the transmitter recess. One embodiment of such pins 5450, in a recess or hole 5410 in the transmitter 5400 that would connect to the sensor set 510 in FIGS. 5A-6C at the connector 524, are shown in FIG. 12. It is preferable to have corrosion resistance at these pins. To achieve better corrosion resistance, for example, cleaning of the pins can take place in an analyte. The pins may be made of a number of different conductive materials that reduce corrosion. Gold plated beryllium copper (BeCu) may be used, for example. The pins may be stamped or formed in another method that reduces surface cracks and improves plating. The transmitter pins are preferably durable and rigid to prevent separation from the connection or other distortion that disturbs transfer of electric current or results in damage to the pins.

Figure 13A:
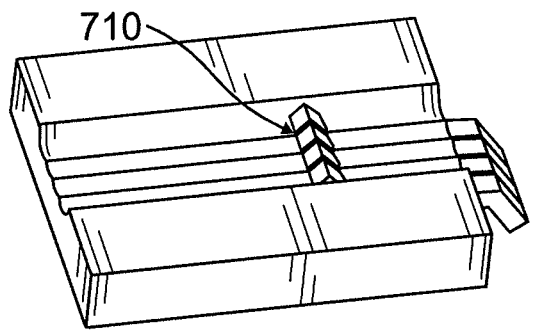
FIGS. 13A-C provide perspective views of stamped pins on the sensor in accordance with an embodiment of the present invention.
Figure 13B:
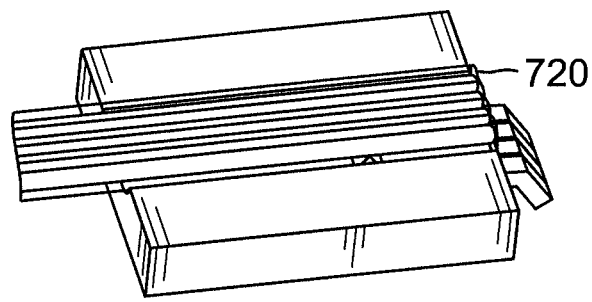
Figure 13C:
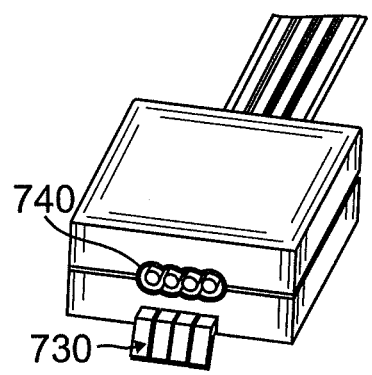

The sensor itself terminates at conductive contacts at the opposite end from the sensing elements. The wires may be stripped such that contacts are exposed and may contact the transmitter pins in order to transfer signals from the sensor to the transmitter pins. While the term "transmitter pins" is used herein, it is understood that the pins could be located on a connector or wire that leads to the transmitter or a monitor, or on a monitor without transmission capability. To eliminate the need to strip wires, a stamped metal insert may be molded into plastic that is part of the sensor set or transmitter. The stamped metal insert would then pierce the wire jacket of the sensor. One such embodiment of the sharp pins 710 that can pierce the wire jacket is showed in FIG. 13A. FIG. 13B shows the wire sensor 720 on top of the sharp pins. A separate connector can also be used for this purpose, where the connector is separate from the transmitter and from the sensor set. Preferably, the connector would be attached during assembly and become a part of the sensor set so that the user only has the sensor set and transmitter to attach without any other pieces. The sharp pins 710 may be electrically connected to stamped sensor pins 740 that fold up and interface to the connection with the transmitter. In further embodiments, the pins may deform as the sensor set is attached to the transmitter, creating the electrical connection between the two. FIGS. 13A-C also show conductive pins 730, which may be stamped or otherwise formed from a metal or other conductive material. These conductive pins are electrically connected to the wires of the sensor such that the signals from the sensor electrode areas can pass through them to the transmitter or other connected device or wire that attaches to the mounting base. In further embodiments, as shown in FIG. 13C, the conductive pins 730 may be disconnected from the wire contacts until the transmitter or other connected device or wire is attached to the mounting base. When the mounting device is connected, the conductive pins 730 deform and contact the wire contacts 740, creating an electrical connection.

In further embodiments, there may be staggered, open areas on the sensor. For example, in the ribbon cable configuration, the staggered, open areas could be opened through laser machining or other mechanical or chemical processes and would then be placed in contact with metal traces, flex circuit traces, photopatternable insulator films, or stamped/formed metal connectors that lead to the contacts or stamped sensor pins that connect to the transmitter pins. These staggered, open areas can be bonded to or just in mechanical contact with the traces or other connecting lines, such that the signals from the sensor can reach the transmitter.

D. Embodiments of the Invention and Associated Characteristics

Embodiments of the invention disclosed herein focus on implantable analyte sensors and sensor systems that are designed to include elements and/or configurations of elements that facilitate sensor initialization and/or start-up in vivo (e.g. the run-in time that it takes for a sensor to settle into its environment and start transmitting meaningful information after being implanted in vivo). In particular, it is known in the art that the amount time required for sensor initialization and/or start-up prior to its use can be relatively long (e.g. in amperometric glucose sensors, the sensor start-up initialization times can range from 2 to 10 hours), a factor which can hinder the use of such sensors in the administration of medical care. For example, in hospital settings, a relatively long sensor initialization and/or start-up period can delay the receipt of important information relating to patient health (e.g. hyperglycemia or hypoglycemia in a diabetic patient), thereby delaying treatments predicated on the receipt of such information (e.g. the administration of insulin). In addition, a relatively long sensor initialization and/or start-up period in hospital settings can require repeated monitoring by hospital staff, a factor which contributes to the costs of patient care. For these reasons, sensors having reduced initialization and/or start-up times in vivo in hospital settings and sensors and sensor systems that are designed to include elements and/or configurations of elements that diminish long sensor initialization and/or start-up times are highly desirable. With glucose sensors for example, a 15-30 minute reduction of sensor initialization and/or start-up time is highly desirable because, for example, such shorter initialization times can: (1) reduce the need for patient monitoring by hospital personnel, a factor which contributes to the cost-effectiveness of such medical devices; and (2) reduce delays in the receipt of important information relating to patient health.

In individuals using analyte sensors in non-hospital settings (e.g. diabetics using glucose sensors to manage their disease), relatively long sensor initialization and/or start-up periods are also problematical due to both the inconvenience to the user as well as the delayed receipt of information relating to user health. The use of glucose sensors, insulin infusion pumps and the like in the management of diabetes has increased in recent years due for example to studies showing that the morbidity and mortality issues associated with this chronic disease decrease dramatically when a patient administers insulin in a manner that closely matches the rise and fall of physiological insulin concentrations in healthy individuals. Consequently, patients who suffer from chronic diseases such as diabetes are instructed by medical personnel to play an active role in the management of their disease, in particular, the close monitoring and modulation of blood glucose levels. In this context, because many diabetics do not have medical training, they may forgo optimal monitoring and modulation of blood glucose levels due to complexities associated with such management, for example, a two hour start-up period which can be an inconvenience in view of a patient's active daily routine. For these reasons, sensors and sensor systems that are designed to include elements and/or configurations of elements can reduce sensor initialization and/or start-up times in are highly desirable in situations where such sensors are operated by a diabetic patient without medical training because they facilitate the patient's convenient management of their disease, behavior which is shown to decrease the well known morbidity and mortality issues observed in individuals suffering from chronic diabetes.

Embodiments of the invention disclosed include those having at least one element within a constellation of elements that have identified as functioning to reduce sensor start-up initialization times. In addition, as disclosed herein, certain embodiments of the invention include those having at least two distinct elements disclosed herein that are within constellation of elements that Applicants have identified as reducing sensor start-up initialization times in a complementary manner. Specifically, not all sensor materials, elements, architectures and/or electronics known in the art can be combined together in a manner that functions to reduce sensor start-up initialization times. Consequently, the disclosure provided herein focuses on those sensor materials, elements, architectures and/or electronics that we have discovered can be combined together to reduce sensor start-up initialization times without antagonizing and/or inhibiting the specific functions of the individual elements.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

The invention disclosed herein has a number of embodiments. One illustrative embodiment of the invention is an analyte sensor apparatus comprising: analyte sensor apparatus comprising: An analyte sensor apparatus comprising: a plurality of electrically conductive sensor wires each having a first end and second end and each arranged in a substantially common orientation, the plurality of sensor wires including a first sensor wire substantially covered by a first electrically insulating cover, wherein an aperture in the first electrically insulating cover defines a working electrode area, a second sensor wire substantially covered by a second electrically insulating cover, wherein an aperture in the second electrically insulating cover defines a reference electrode area and a third sensor wire substantially covered by a third electrically insulating cover, wherein an aperture in the third electrically insulating cover defines a counter electrode area. In further embodiments, there are additional wires also arranged in a substantially common orientation. The additional wires may also have electrically insulating covers with apertures defining further electrodes. For example, there may be an additional wire with a second counter electrode. Typical embodiments of the invention are comprised of biocompatible materials and/or have structural features designed for implantation within a mammal. Methodological embodiments of the invention include methods for making and using the sensor embodiments disclosed herein. Certain embodiments of the invention include methods of using a specific sensor element and/or a specific constellation of sensor elements to produce and/or facilitate one or more functions of the sensor embodiments disclosed herein.

In certain embodiments of the invention, the reactive surfaces of the electrodes are of different relative areas/sizes, for example a 1× reference electrode, a 2.6× working electrode and a 3.6× counter electrode. In certain embodiments of the invention, distributed electrode configurations are used in methods designed to overcome problems with sensors and sensor systems that occur due to lack of hydration (e.g. slow start-up initialization times), fluid stagnation, a patient's immune response, or the like. For example, sensor embodiments having a plurality of electrodes disposed on a substrate in a distributed electrode configurations are observed to exhibit a better start-up profile than sensors having a single set of electrodes disposed on a substrate in a longitudinal row. In addition, embodiments of the invention having distributed electrode configurations can be combined with certain complementary elements disclosed herein so as to further overcome problems that result from a lack of hydration, fluid stagnation, a patient's immune response, or the like (e.g. multiple electrode sensors, voltage pulsing methods etc.).

Another embodiment of the invention also designed to address the lack-of-electrode hydration and/or fluid stagnation etc. is a sensor configured to facilitate in vivo fluid flow to the electrode, for example by removing tubing and/or cover elements that surrounding the sensor, which, as shown herein, optimizes sensor initialization without compromising long-term function of implantable sensors (e.g. as could result from biofouling of the exposed sensor surfaces). For example in certain sensor embodiments having tubing surrounding the reference electrode, the startup rate without that trimming can be as low as 60%. If, however, the sidewalls of the tubing surrounding the reference electrode are trimmed in such embodiments, 100% of the sensors startup. In such embodiments of the invention, the removal of a sidewall may facilitate hydration, and/or allow closer proximity of tissue and/or reduce the likelihood of fluid stagnation. In this context, embodiments of the invention include those having a constellation of elements arranged in a manner designed not to inhibit (and optional to enhance) flow of a fluid containing an analyte of interest around/ through the elements of the sensor embodiment to a reactive surface of an electrode of the sensor embodiment.

Figure 9:
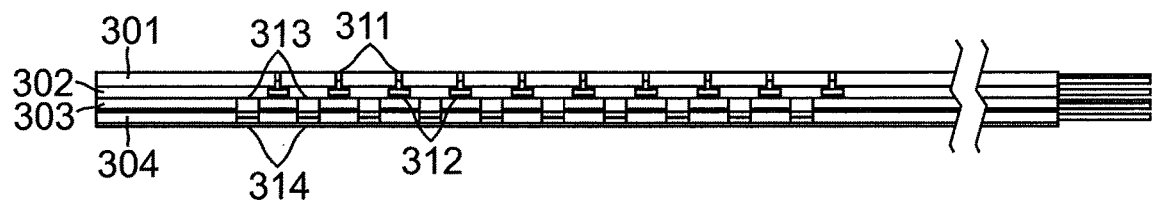
FIG. 9 provides a diagrammatic view of a distributed electrode configured wire sensor according to an embodiment of the present invention.

In one embodiment of the invention, a working electrode, a counter electrode and a reference electrode are positionally distributed on the sensor wires in a configuration that facilitates hydration of the working electrode, the counter electrode or the reference electrode when the sensor apparatus is placed in contact with a fluid comprising the analyte (e.g. by inhibiting shadowing of the reference electrode, a phenomena which can inhibit hydration and capacitive start-up of a circuit). Optionally, for example the sensor includes a distributed electrode configuration and/or an aperture configuration that inhibits the occurrence of localized and detrimental environment changes around a single electrode (e.g. inactivation of some portion of the electrode function due to bubble formation, and/or an in vivo response such as biofouling and/or an immune response). Typically such embodiments of the invention facilitate sensor start-up or initialization. Illustrative embodiments of such electrode configurations are shown in FIG. 9.

Typical analyte sensor apparatus embodiments may comprise a plurality of working electrodes, counter electrodes and reference electrodes. Optionally, the plurality of working, counter and reference electrodes on their respective wires are grouped together as a unit and positionally distributed on the wires in a repeating pattern of units. Alternatively, the plurality of working, counter and reference electrodes are grouped together and positionally distributed in a non-repeating pattern of units. In some embodiments, the electrodes are grouped in a configuration that allows the sensor to continue to maintain an optimal function if a portion of the sensor having one or more electrodes is dislodged from an in vivo environment and exposed to an ex vivo environment.

Related embodiments of the invention include methods for using a material at the aperture that is designed to facilitate the hydration and/or initialization of various sensor embodiments of the invention. For example, in certain embodiments of the invention, a portion of the sensor apparatus such as one or more apertures is coated and/or filled with a hydrophilic composition (e.g. a hydrophilic polymer) so as to facilitate fluid flow through the one or more apertures. Optionally, the hydrophilic composition further comprises a bioactive agent such as an anti-thrombocytic, anti-inflammatory or anti-proliferative agent (see, e.g. U.S. Pat. No. 6,770,729, the contents of which are incorporated by reference). Because the in vivo thrombocytic, inflammatory and/or proliferative response can deposit cells and other biological materials on or near the sensor that can decrease fluid flow to the sensor, hydrophilic polymers containing these bioactive agents can be used in methods designed to facilitate the hydration and/or initialization of various sensor embodiments of the invention. In certain embodiments of the invention, the bioactive agent can elute from the sensor and migrate into the in vivo environment (e.g. anti-inflammatory agents such as dexamethasone). In other embodiments of the invention, the bioactive agent does not elute from the sensor (e.g. agents such as metallic silver, inorganic silver compounds, silver salts of organic acids, or the like).

In certain embodiments of the invention, sensor systems that comprise an aperture configuration disclosed herein are used in methods designed to overcome problems that can occur with implantable sensors and sensor systems due to lack of hydration (e.g. slow start-up initialization times) and/or fluid stagnation by enhancing the ability of a fluid to flow around the implanted components in a manner that inhibits the likelihood of a gas bubble or a stagnating pool of fluid from forming and/or remaining on top of or close to an electrode in a manner that compromises sensor function. In addition, embodiments of the invention that specific aperture configurations can be combined with certain complementary elements disclosed herein so as to further overcome problems that result from a lack of hydration, fluid stagnation, a patient's immune response, or the like (e.g. distributed electrode configurations, multiple electrode sensors, multiple sensor apparatuses having multiple implantation sites, voltage pulsing methods etc.).

Various elements of the sensor apparatus can be disposed at a certain location in the apparatus and/or configured in a certain shape and/or be constructed from a specific material so as to facilitate strength, hydration and/or function of the sensor. In certain embodiments of the invention, the structural features and/or relative position of the working and/or counter and/or reference electrodes is designed to influence sensor manufacture, use and/or function. One such embodiment of the invention includes electrodes having one or more rounded edges so as to inhibit delamination of a layer disposed on the electrode (e.g. an analyte sensing layer comprising glucose oxidase). Illustrative embodiments of such rounded electrodes are shown in U.S. patent application Ser. No. 12/184,117, filed on Jul. 31, 2008, which is herein incorporated by reference. Related embodiments of the invention include methods for inhibiting delamination of a sensor layer using a sensor embodiments of the invention (e.g. one having one or more electrodes having one or more rounded edges).

In some embodiments of the invention, a barrier element is disposed on the apparatus so as to inhibit spreading of a layer disposed on an electrode. Illustrative embodiments of such barrier/dam structures are shown in U.S. patent application Ser. No. 12/184,117, filed on Jul. 31, 2008, which is herein incorporated by reference. Optionally, an element such as a metallic or other structure is disposed on top of the dam structure(s). Related embodiments of the invention include methods for inhibiting movement of a compound disposed on a sensor embodiments of the invention (e.g. one constructed to have such a barrier structure). Optionally, a barrier element is disposed on the apparatus so as to encircle a reactive surface of an electrode. Such barrier elements can be made from a variety of materials, for example a polyimmide. In various embodiments of the invention, these elements can be formed as part of the electrode or alternatively bonded to the electrode after it is formed (e.g. using an epoxy or the like).

The sensors may comprise a series of electrodes disposed on a base of wires such as a ribbon cable, bundled wire configuration, or stacked wire configuration. These configurations are useful in manufacturing/production of the sensor, for example those processes that involve progressive laser ablation. In one such embodiment, a pattern of laser ablation is controlled to produce a single wire with one or more working, counter and reference electrodes and/or a plurality of such electrode groups. Optionally this is in a reel form that is cut into segments prior to sensor manufacture. One illustrative embodiment of this design comprises a wire electrode with multiple reading points (e.g. perforations) along its wire/ribbon body. This wire can further be disposed within sheath or tube having a plurality of windows. Subsequent layers such as the analyte modulating layer can be coated over a portion of, or alternatively, the whole wire. Related embodiments of the invention include a method of making such sensors, wherein a step in the method includes disposing the wire electrode in the form of a reel that is then cut into segments during the manufacturing process.

In addition, electrodes in various embodiments of the invention can be coated with a variety of materials (e.g. an analyte modulating layer) in order to influence the function of the sensor apparatus. In some embodiments of the invention, a hydrophilic analyte modulating layer is coated over at least 50, 75% or 100% of the reactive surface of an electrode (e.g. an electrically conductive wire). For example certain embodiments of the invention disclosed herein (e.g. amperometric glucose sensors) include elements and/or constellations of elements that are designed to overcome what is known as "oxygen deficit problem." This problem relates to the fact in that sensors designed to measure an analyte via the reaction of an analyte and oxygen, the oxygen concentration must be in excess. If the oxygen is not in excess (and is instead the rate limiting reactant), the sensor signal will be proportional to the oxygen concentration and not the analyte, which the sensor is designed to measure. Under these conditions, sensors will not function properly. Therefore, there is a need for sensors that include biocompatible membrane with differential oxygen and analyte permeabilities (e.g. glucose limiting membranes) and further having elements that function to enhance sensor initialization start up time and further.

Optionally, embodiments of the invention include a plurality of working electrodes and/or counter electrodes and/or reference electrodes (e.g. to provide redundant sensing capabilities). Such embodiments of the invention can be used in embodiments of the invention that include a processor (e.g. one linked to a program adapted for a signal subtraction/cancellation process) are designed factor out background signals in vivo, for example by comparing signal(s) at GOx coated working electrode with signal at working electrode not coated with GOx (e.g. background detection followed by a signal subtraction/cancellation process to arrive at a true signal). Certain of these embodiments of the invention are particularly useful for sensing glucose at the upper and lower ends of the glucose signal curves. Similar embodiments of the invention are used to factor out interference, for example by comparing signal(s) at GOx coated working electrode with signal at working electrode not coated with GOx. Embodiments of the invention can include a coating of a Prussian blue composition on an electrode at a location and in an amount sufficient to mediate an electrical potential of an electrode of the apparatus. Related embodiments of the invention include methods for mediating an electrical potential of an electrode of the disclosed sensor apparatus (e.g. by using a Prussian blue composition). Prussian Blue formulas are known in the art and include $Fe_4[Fe(CN_6]_3 \times H_2O$, CI no. 77510 and $KFe[Fe(Cn)_6] \times H_2O$ id CI no. 77520.

In some embodiments of the invention, the architecture or thickness of the chemistry layer(s) is used to optimize a property of the sensor. In some embodiments of the invention, the analyte modulating layer is at least 6, 7, 8, 9, 10, 15, 20, 25 or 30 microns thick. Certain embodiments of the invention use a thick layer (e.g. 25 or 30 microns) of an analyte modulating layer because in such embodiments, this thick layer is observed to both optimize the linearity of an analyte signal over a range of signals (e.g. glucose concentration). Such thick layers have further properties that are desirable in certain embodiments of the invention, for example a longer analyte modulating layer lifetime (e.g. due to the extra material), a property that makes them particularly suited for certain long term sensor embodiments.

Typical embodiments of the invention comprise further layers such as an adhesion promoting layer disposed between the analyte sensing layer and the analyte modulating layer. Optionally in such embodiments, a first compound in the adhesion promoting layer is crosslinked to a second compound in the analyte sensing layer. Certain embodiments of the invention include an interference rejection layer, for example one comprised of a NAFION (a sulfonated tetrafluoroethylene copolymer having the molecular formula $C_7HF_{13}O_5S \cdot C_2F_4$, CAS number [31175-20-9]) and/or a cellulose acetate composition. An illustrative embodiment of an interference rejection membrane (IRM) comprising NAFION and its effectiveness at inhibiting interfering signals that can be generated by acetaminophen in an amperometric sensor is shown in FIG. 10. Typically, an IRM is disposed under an analyte sensing layer (e.g. one comprising glucose oxidase). In certain embodiments of the invention, the IRM is disposed between the reactive surface of an electrode and an analyte sensing layer. Related embodiments of the invention include methods for inhibiting one or more signals generated by an interfering compound in various sensor embodiments of the invention (e.g. by using an interference rejection layer).

In typical embodiments of the invention, the sensor is operatively coupled to further elements (e.g. electronic components) such as elements designed to transmit and/or receive a signal, monitors, pumps, processors and the like. For example, in some embodiments of the invention, the sensor is operatively coupled to a sensor input capable of receiving a signal from the sensor that is based on a sensed physiological characteristic value in the mammal; and a processor coupled to the sensor input, wherein the processor is capable of characterizing one or more signals received from the sensor. A wide variety of sensor configurations as disclosed herein can be used in such systems. Optionally, for example, the sensor comprises three working electrodes, one counter electrode and one reference electrode. In certain embodiments, at least one working electrode is coated with an analyte sensing layer comprising glucose oxidase (and optionally two are coated with GOx) and at least one working electrode is not coated with an analyte sensing layer comprising glucose oxidase. Such embodiments of the invention can be used for example in sensor embodiments designed factor out background signals in vivo, for example by comparing signal(s) at GOx coated working electrode(s) with signal at working electrode(s) not coated with GOx (e.g. background detection followed by a signal subtraction/cancellation process to arrive at a true signal).

Embodiments of the invention include sensors and sensor systems having configurations of elements and/or architectures that optimize aspects of sensor function. For example, certain embodiments of the invention are constructed to include multiple and/or redundant elements such as multiple sets of sensors and/or sensor system elements such as multiple piercing members (e.g. needles) and/or a cannulas organized on an insertion apparatus for use at a patient's in vivo insertion site. One embodiment of the invention is a dual piercing member or "fang" sensor system embodiment. This embodiment of the invention is a sensor apparatus for monitoring a body characteristic of the patient, the apparatus comprising a base element adapted to secure the apparatus to the patient, a first piercing member that is coupled to and extending from the base element, wherein the first piercing member is operatively coupled to (e.g. to provide structural support and/or enclose) at least one first electrochemical sensor having at least one electrode for determining at least one body characteristic of the patient at a first sensor placement site, as well as a second piercing member that is coupled to and extending from the base element and operatively coupled to at least one second electrochemical sensor having at least one electrode for determining at least one body characteristic of the patient at a second sensor placement site. In some embodiments of the invention, such sensor systems are used in a hospital setting such as in an intensive care unit (e.g. to measure blood glucose concentrations in the interstitial fluid or blood of a diabetic patient). In other embodiments of the invention, the apparatus is used in an ambulatory context, for example by a diabetic in the daily monitoring of blood glucose. The dual piercing embodiments are disclosed in more detail in U.S. patent application Ser. No. 12/184,117, filed on Jul. 31, 2008, which is incorporated herein by reference.

Embodiments of the invention can include a plurality of sensors coupled to a single piercing member in a manner that allows them to be disposed together in vivo at a single insertion site. For example, see U.S. patent application Ser. No. 12/184,117, filed on Jul. 31, 2008, which is incorporated herein by reference.

Embodiments of the invention that include a plurality of sensors can overcome a variety of problems observed to occur with single sensors by providing multiple physiological characteristic readings at multiple insertion sites in a manner that compensates for or overcomes an occurrence of one or more of the above noted problems at a single insertion site. For example, by using embodiments of the invention constructed to include these elements, an immune response or problematical anatomical feature (e.g. scar tissue) at a single insertion site will not compromise the function of the multiple sensor apparatus in view of the multiple/redundant sensor signals that are provided by such embodiments of the invention. In addition, embodiments of the invention that include a plurality of sensors can use the multiple sensor signals to characterize, compensate for and overcome problems associated with "drift" that can occur with a single sensor at a single insertion site (i.e. the phenomena where an output signal of the sensor changes over time independent of the measured property). Embodiments of the invention that include a plurality of sensors can be combined with other sensor elements and/or configurations disclosed herein in order to further optimize sensor function and can comprise for example electrodes distributed in a configuration that enhances the flexibility of the sensor structure and/or facilitates hydration of the sensor electrodes. Similarly, these embodiments of the invention can be combined with the apparatuses and methods that use voltage switching and/or pulsing as part of the initialization and/or sensing process as discussed in detail below.

As noted above, certain embodiments of the invention can use voltage switching as part of the sensing process. Embodiments of the invention can use voltage switching not only in the detection of interfering species and/or specific analyte concentrations but also to facilitate the hydration and/or initialization of various sensor embodiments of the invention. In particular, the time for initialization ("run-in") differs for different sensors and can take hours. Embodiments of the invention include a sensor initialization scheme involving high frequency initialization (switching of voltage potentials). In one illustrative embodiment, a triple initialization profile is used where the voltage of the sensor is switched between a first potential such as 0, 280, 535, 635 or 1.070 millivolts and a second potential such as 0, 280, 535, 635 or 1.070 millivolts over a period of 5, 10, 20, 30 or 45 seconds or 1, 5, 10 or 15 minutes. Certain voltage switching embodiments of the invention further use voltage pulsing in the detection of analyte signals. The number of pulses used in such embodiments of the invention is typically at least 2 and can be 3, 4, 5, 6, 7, 8, 9, 10, 15, 20 or more. Pulses can be for a predetermined period of time, for example 1, 3, 5, 7, 10, 15, 30, 45, 60, 90 or 120 seconds. One illustrative example of this comprises 6 pulses, each a few seconds long. By using such embodiments of the invention, the sensor run-in is greatly accelerated, a factor which optimizes a user's introduction and activation of the sensor. Certain of these methods can be adapted for use with similar methods known in the art (see, e.g. U.S. Pat. Nos. 5,320,725; 6,251,260 and U.S. Patent Application No. 2005/0161346, the content of which are incorporated by reference).

In some embodiments of the invention, a pulsed (e.g. produced or transmitted or modulated in short bursts or pulses) voltage is used to obtain a signal from one or more electrodes of the sensor. In related embodiments of the invention, the use of a pulsed current or the like is used. Such pulsing for example can be used to reduce/compensate for background current readings. Further discussion of this type of pulsing and the benefits of such pulsing can be seen, for example, in U.S. patent application Ser. No. 12/184,117, filed on Jul. 31, 2008, which is herein incorporated by reference.

A variety of different voltage pulsed and/or voltage switched sensor embodiments are contemplated. In this context, sensor systems can include a processor including software algorithms that control factors such as voltage output and/or working potential and/or pulsing and or switching and/or the time periods of such factors. Sensor systems can also include various hardware features designed to facilitate voltage pulsing, for example discharge circuit elements. In particular, in certain embodiments of the invention, high frequency switching can require a discharge circuit element so that layers discharge held charge (wherein the sensor layers analogous to a capacitor). One illustrative embodiment is sensor having two specific potential dedicated electrodes (e.g. at 280 mv and 535 mv) and is designed to obtain readings of both electrodes as sensor switches between them. In this context, it is known in art to take sensor reading at a wide range of potentials (see, e.g. U.S. Pat. Nos. 5,320,725, 6,251,260, 7,081,195 and Patent Application No. 2005/0161346). In one illustrative embodiment of the invention, a processor is used to observing signals obtained from one of two working electrodes in a sensor via a pulsed voltage and comparing it to the signal obtained from the second working electrode, wherein this second working electrode is not exposed to a pulsed voltage.

In some embodiment of the invention, a sensor functions by applying a first voltage for a first time to initiate an anodic cycle in the sensor, by applying a second voltage for a second time to initiate a cathodic cycle in the sensor, and repeating the application of the first voltage and the second voltage to continue the anodic-cathodic cycle in the sensor. In an embodiment of the invention, a sensor may function by applying a first voltage for a first time, by waiting a predetermined period of time (i.e., not applying a voltage), and then cycling between the application of the first voltage and the waiting of a predetermined period of time for a number of iterations or a specific timeframe. The first voltage may have a positive value or a negative value. The second voltage may have a positive value or negative value. Under certain operating conditions, a voltage magnitude of the first voltage for one of the iterations may have a different magnitude from a voltage magnitude of the first voltage for a second or different iteration. In an embodiment of the invention, a voltage waveform, such as a ramp waveform, a stepped waveform, a sinusoid waveform, and a squarewave waveform, may be applied as the first voltage. Any of the above mentioned waveforms may also be applied as the second voltage. Under certain operating conditions, the voltage waveform applied as the first voltage in a first iteration may differ from the voltage waveform applied as the first voltage in the second iteration. The same may hold true for the application of the second voltage. Under certain operating conditions, a voltage waveform may be applied as the first voltage to the sensor and a voltage pulse may be applied as the second voltage to the sensor.

In an embodiment of the invention, a plurality of short duration voltage pulses are applied for the first timeframe to initiate the anodic cycle in the sensor. In such embodiments, a plurality of short duration voltage pulses may be applied for the second timeframe to initiate the cathodic cycle in the sensor. The magnitude of the first plurality of short duration pulses may be different from the magnitude of the second plurality of short duration pulses. In an embodiment of the invention, the magnitude of some of the pulses in the first plurality of short duration pulses may have different values from the magnitude of other pulses in the first plurality of short duration pulses. The shorter duration voltage pulses may be utilized to apply the first voltage, the second voltage, or both. In an embodiment of the present invention, the magnitude of the shorter duration voltage pulse for the first voltage is −1.07 volts and the magnitude of the shorter duration voltage pulse for the second voltage is approximately half of the high magnitude, e.g., −0.535 volts. Alternatively, the magnitude of the shorter duration pulse for the first voltage may be 0.535 volts and the magnitude of the shorter duration pulse for the second voltage is 1.07 volts.

In embodiments of the invention utilizing short duration pulses, the voltage may not be applied continuously for the entire first time period. Instead, in the first time period, the voltage application device may transmit a number of short duration pulses during the first time period. In other words, a number of mini-width or short duration voltage pulses may be applied to the electrodes of the sensors over the first time period. Each mini-width or short duration pulse may a width of a number of milliseconds. Illustratively, this pulse width may be 30 milliseconds, 50 milliseconds, 70 milliseconds or 200 milliseconds. These values are meant to be illustrative and not limiting.

In another embodiment of the invention, each short duration pulse may have the same time duration within the first time period. For example, each short duration voltage pulse may have a time width of 50 milliseconds and each pulse delay between the pulses may be 950 milliseconds. In this example, if two minutes is the measured time for the first timeframe, then 120 short duration voltage pulses may be applied to the sensor. In an embodiment of the invention, each of the short duration voltage pulses may have different time durations. In an embodiment of the invention, each of the short duration voltage pulses may have the same amplitude values. In an embodiment of the invention, each of the short duration voltage pulses may have different amplitude values. By utilizing short duration voltage pulses rather than a continuous application of voltage to the sensors, the same anodic and cathodic cycling may occur and the sensor (e.g., electrodes) is subjected to less total energy or charge over time. The use of short duration voltage pulses utilizes less power as compared to the application of continuous voltage to the electrodes because there is less energy applied to the sensors (and thus the electrodes).

In certain embodiments of the invention, sensor systems that utilize voltage pulsing and/or switching as disclosed herein are used in methods designed to overcome problems that can occur with implantable sensors and sensor systems due to lack of hydration (e.g. slow start-up initialization times) and/or fluid stagnation by enhancing the ability of a fluid to flow around the implanted components in a manner that inhibits the likelihood of a gas bubble or a stagnating pool of fluid from forming and/or remaining on top of or close to an electrode in a manner that compromises sensor function. In addition, embodiments of the invention that utilize voltage pulsing and/or switching can be combined with certain complementary elements disclosed herein so as to further overcome problems that result from a lack of hydration, fluid stagnation, a patient's immune response, or the like (e.g. distributed electrode configurations, multiple electrode sensors, multiple sensor apparatuses having multiple implantation sites, etc.).

Some embodiments of the invention include a fuse element that can be triggered after a predetermined period of time or event so as to interrupt a flow of electrical current within the apparatus (i.e. so as to disable the sensor). For example, one embodiment of the invention includes a sensor operatively coupled to a sensor input capable of receiving a signal from the sensor that is based on a sensed physiological characteristic value in the mammal; and a processor coupled to the sensor input, wherein the processor is capable of triggering a fuse element to disable the sensor after a predetermined period which is based upon the in vivo lifetime of the sensor. In a related embodiments of the invention, the processor is capable of triggering a fuse element upon receipt of a signal that is outside of a predetermined set of signal parameters that are associated with normal sensor function. In one such embodiment of the invention, parameters that are outside of those associated with normal sensor function includes a current that is above a prescribed maximum or is below a prescribed minimum for more than a prescribed time. Related embodiments of the invention include methods for disabling a sensor embodiments of the invention (e.g. by using a fuse element), for example a sensor which has exceeded a predetermined period of operation (e.g. lifespan) and/or a sensor that is not performing within a predetermined set of operating parameters. A variety of fuse elements known in the art can be adapted for use with the sensor embodiments disclosed herein. One illustrative embodiment of a fuse element is shown in U.S. patent application Ser. No. 12/184,117, filed on Jul. 31, 2008, which is herein incorporated by reference.

Certain sensor embodiments that include a fuse element can include a plurality of fuse elements, that for example can be triggered individually by different events. In one illustrative embodiment of the invention that comprises two fuse elements, both of which must be triggered to disable sensor function, a first fuse element is triggered upon initialization of start-up of the sensor; and the second fuse element is triggered after a certain time period, for example 1, 3, 5, 7, 14, 21 or 30 days. Such embodiments of the invention are useful for example to prevent a user from using the sensor in vivo longer than its appropriate lifetime. Other embodiments of the invention having a fuse element can be constructed to trigger a fuse upon being connected/disconnected to a circuit and used for example to prevent users from disconnecting and/or reconnecting the sensor. Some embodiments of the invention further comprise a discharge circuit element (e.g. a switch) and/or a potentiostat operatively coupled to the sensor to facilitate an electrical discharge from the sensor. In certain embodiments of the invention, sensor systems that utilize fuse elements as disclosed herein are used in methods designed to overcome problems that can occur with the use of a sensor past its approved lifetime and/or sensor malfunction. One illustrative methodological embodiment is a method of preventing a sensor from: (1) functioning past its approved lifetime: and/or (2) providing readings to a user while malfunctioning comprising by coupling the sensor to a fuse element that is designed to trigger and turn off sensor function after a predetermined time period and/or the sensor performs outside of a predetermined set of operating parameters.

In some embodiments of the invention, a processor is capable of comparing a first signal received from a working electrode in response to a first working potential with a second signal received from a working electrode in response to a second working potential, wherein the comparison of the first and second signals at the first and second working potentials can be used to identify a signal generated by an interfering compound. In one such embodiment of the invention, one working electrode is coated with glucose oxidase and another is not, and the interfering compound is acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides or uric acid. Optionally, a pulsed and/or varied (e.g. switched) voltage is used to obtain a signal from a working electrode. Typically, at least one voltage is 280, 535 or 635 millivolts. Related embodiments of the invention include methods for identifying and/or characterizing one or more signals generated by an interfering compound in various sensor embodiments of the invention (e.g. by comparing the signal from an electrode coated with an analyte sensing compound with a comparative electrode not coated with an analyte sensing compound). Optionally, such methods use a pulsed and/or varied working potential to observe a signal at an electrode. An amperometric glucose sensor detects an interfering signal generated by acetaminophen at an operating potential of 535 mV and further that this interfering signal is suppressed when the sensor is switched to an operating potential 280 mV. This data shows that reducing the operating potential from 535 mV to 280 mV suppresses signals generated by acetaminophen over a range of glucose concentrations (0-400 mg/dL). In addition, this data shows that the reduced operating potential allows the sensor to maintain the 535 mV equivalent linearity.

In a related embodiment of the invention, a processor compares a first signal received from a working electrode coated with glucose oxidase in response to a first working potential with a second signal received from a working electrode coated with glucose oxidase in response to a second working potential, wherein the comparison of the first and second signals at the first and second working potentials is used to characterize a blood glucose concentration within at least one discreet concentration range. In certain embodiments of the invention at least two working potentials of approximately 280, 535 or 635 millivolts is used. In some embodiments of the invention, the comparison of the first and second signals at the first and second working potentials can be used to characterize a blood glucose concentration within a concentration range below 50 or 70 mg/dL (i.e. values typically associated with hypoglycemia) or above 125, or 150 mg/dL (i.e. values typically associated with hyperglycemia). In certain embodiments of the invention a 280 mv potential is used because it can detect lower concentrations of glucose more efficiently. Related embodiments of the invention include methods for identifying and/or characterizing a specific analyte concentration or range of analyte concentrations using the various sensor embodiments of the invention (e.g. by comparing the analyte signal from one or more electrodes at different working potentials, wherein the different working potentials are selected for their ability to characterize a specific analyte concentration and/or range of analyte concentrations).

In another illustrative embodiment of the invention, the processor is capable of characterizing a plurality of signals received from the sensor by for example comparing a first signal received from a working electrode coated with glucose oxidase with a second signal received from a working electrode not coated with glucose oxidase so as to obtain information on a background signal that is not based on a sensed physiological characteristic value in the mammal. In another illustrative embodiment of the invention, the processor is capable of characterizing a plurality of signals received from the sensor by comparing a first signal received from a working electrode coated with glucose oxidase with a second signal received from a working electrode not coated with glucose oxidase so as to obtain information on a signal generated by an interfering compound. In another embodiment of the invention, two working electrodes are coated with glucose oxidase and the processor is capable of obtaining information on glucose concentrations in the mammal by comparing the signals received from the two working electrodes coated with glucose oxidase.

Certain sensor embodiments that switch between a high potential to a low potential (e.g. with a frequency of less than 3, 2 or 1 seconds). In such embodiments, a sensor may not discharge, with for example sensor elements acting as a sort of capacitor. In this context, some embodiments of the invention can include a circuit discharge element that facilitates sensor circuit discharge (e.g. if discharge is not sufficient to reach a specific potential such as 535 millivolts). A variety of such circuit discharge elements known in the art can be adapted for use with sensor embodiments of the invention (see, e.g. U.S. Pat. Nos. 4,114,627; 4,373,531; 4,858,610; 4,991,583; and 5,170,806, 5,486,201, 6,661,275 and U.S. Patent Application No. 20060195148). Optionally for example, a sensor charge can be removed by connecting it through a discharging switch element, and optionally a discharging resistor element.

Certain embodiments of the invention include a processor that detects whether a sensor is sufficiently hydrated for analyte detection comprising a computer usable media including at least one computer program embedded therein that is capable of calculating an impedance value; and comparing the impedance value against a threshold to determine if the sensor is sufficiently hydrated for analyte detection. A related embodiment of the invention is a method of detecting whether a sensor is sufficiently hydrated for analyte detection, comprising calculating an open circuit potential value between at least two electrodes of the sensor; and comparing the open circuit potential value against a threshold to determine if the sensor sufficiently hydrated for analyte detection. Typically, the open circuit potential value is the impedance value (and optionally this value is an approximation of a sum of polarization resistance and solution resistance). Optionally, the open circuit potential value is compared against an another threshold to determine if the sensor sufficiently hydrated for analyte detection. This can solve problems that occur when a user attempts to initialize a sensor that is not fully hydrated (e.g. compromising the accuracy and/or lifetime of the sensor).

As noted above, it has been discovered that certain crosslinking reagents can be used for example to produce crosslinked polypeptide layers having a constellation of structural and chemical properties that make them surprisingly useful in certain contexts (e.g. when used to crosslink carrier proteins such albumin and enzymes such as glucose oxidase within a layer of a sensor apparatus having a plurality of overlapping functional layers). As is known in the art, crosslinking is the process of chemically joining two or more molecules by a covalent bond. Crosslinking compounds typically comprise a linker "arm" that functions as a tether between crosslinked compounds as well as at least two chemical moieties (typically on distal ends of the arm of the compound) that react specific functional groups on proteins or other molecules (see, e.g. primary amines, sulfhydryls and the like). As discussed in detail below, a variety of crosslinking agents are known and commercially available from suppliers such as Pierce Biotechnology Inc., Rockford, Ill. (see, e.g. bis N-succinimidyl-[pentaethylene glycol]ester, Pierce Product No. 21581).

Crosslinkers can be either homobifunctional or heterobifunctional. Homobifunctional crosslinkers have two identical reactive groups and often are used in one-step reaction procedures to crosslink proteins to each other or to stabilize quaternary structure. Even when conjugation of two different proteins is the goal, one-step crosslinking with homobifunctional reagents can result in self-conjugation, intramolecular crosslinking and/or polymerization. Heterobifunctional crosslinkers possess two different reactive groups that can allow for sequential (two-stage) conjugations, which can for example help to minimize undesirable crosslinking reactions such as polymerization or self-conjugation. Heterobifunctional reagents can be used for example when modification of amines is problematic because for example, amines are sometimes present at the active sites of proteins and modification of these may lead to activity loss. Other moieties such as sulfhydryls, carboxyls, phenols and carbohydrates may be more appropriate targets.

Two-step (i.e. sequential) crosslinking strategies in this context can allows a protein that can tolerate the modification of its amines to be coupled to a protein or other molecule having different accessible groups. In sequential crosslinking procedures, heterobifunctional reagents can be reacted with one protein using the most labile group of the crosslinker first. After removing excess nonreacted crosslinker, the modified first protein is added to a solution containing the second protein where reaction through the second reactive group of the crosslinker occurs. Commonly used heterobifunctional crosslinkers include those having an amine-reactive succinimidyl ester (i.e., NHS-ester) at one end and a sulfhydrylreactive group on the other end. The sulfhydryl-reactive groups are usually maleimides, pyridyl disulfides and α-haloacetyls. The NHS-ester reactivity is less stable in aqueous solution and is usually reacted first in sequential crosslinking procedures. NHS-esters react with amines to form amide bonds.

Carbodiimides are zero-length crosslinkers (see, e.g., EDC, Pierce Product #22980, 22981) and effect direct coupling between carboxylates (—COOH) and primary amines (—NH2) and have been used in protein-protein conjugation. Other heterobifunctional reagents include those compounds having one reactive group that is photoreactive rather than thermoreactive. These compounds can have advantages in protein:protein interaction studies and in cases where the availability of thermoreactive targetable functional groups is unknown. This reactivity allows for specific attachment of the labile thermoreactive group first; subsequently, conjugation to any adjacent N—H or C—H sites may be initiated through the photoreactive group by activation with UV light. The reactivity of the photochemical reagent allows for formation of a conjugate that may not be possible with a group-specific reagent.

Crosslinkers for use in a particular context can be selected on the basis of their chemical reactivities (i.e., specificity for particular functional groups) as well as their compatibility of the reaction with the application (see, e.g. crosslinking a functional glucose oxidase polypeptide with an albumin polypeptide). The specific crosslinker to use in a specific application can be determined empirically. However, crosslinkers can be selected due to previously characterized properties such as one or more of the following: chemical specificity; spacer arm length; reagent water-solubility and cell membrane permeability; same (homobifunctional) or different (heterobifunctional) reactive groups; thermoreactive or photoreactive groups; whether the reagent crosslinks are cleavable or not; whether the reagent contains moieties that can be radiolabeled or tagged with another label. Illustrative crosslinking compounds are shown, for example in U.S. patent application Ser. No. 12/184,046, which is herein incorporated by reference.

As noted above, embodiments of the invention include methods for making the sensor embodiments disclosed herein. Certain methods for making the sensor embodiments disclosed herein include the step of precisely controlling the concentration of a constituent so as to effect its morphology, function or the like. For example in sensors that use GOx, a concentration range of about 20-40 KU (and 5% Human Serum Albumin) can be used to optimize GOx layer morphology. Methods for making the sensor embodiments disclosed herein include the step of applying an oxidoreductase (e.g. a GOx composition) onto the surface of an electrode via brushing methods that facilitate its disposal in proximity to reactive surface. In this context, brushing (e.g. with the equivalent of a tiny paintbrush) GOx onto electrode surface and/or writing GOx onto electrode surface using a pen-type device can be employed rather than depositing a droplet of the solution, a procedure which (e.g. due to surface tension of droplet) can produce uneven deposition. Moreover, such brushing steps can push a composition solution deep into the convoluted reactive surface of a Pt black of electrode. In addition, brushing is easier than processes such as spin coating because it allows for a more precise localized deposition of a composition. In this context, brushing allows for example, the easy coating of small reactive surfaces that are not amenable to coating by other means (e.g. pipetting and/or spin coating processes). Certain embodiments for making the invention can be performed under a vacuum to, for example, pull out air and facilitate application of a layer to a substrate. Certain embodiments for making the invention include the step of performing a crosslinking reaction under a vacuum to pull out air and facilitate application.

As noted above, the sensor embodiments disclosed herein can be used to sense analytes of interest in one or more physiological environments. In certain embodiments for example, the sensor can be in direct contact with interstitial fluids as typically occurs with subcutaneous sensors. The sensors of the present invention may also be part of a skin surface system where interstitial glucose is extracted through the skin and brought into contact with the sensor (see, e.g. U.S. Pat. Nos. 6,155,992 and 6,706,159 which are incorporated herein by reference). In other embodiments, the sensor can be in contact with blood as typically occurs for example with intravenous sensors. The sensor embodiments of the invention further include those adapted for use in a variety of contexts. In certain embodiments for example, the sensor can be designed for use in mobile contexts, such as those employed by ambulatory users (e.g. a diabetic performing daily activities). Alternatively, the sensor can be designed for use in stationary contexts such as those adapted for use in clinical settings. Such sensor embodiments include, for example, those used to monitor one or more analytes present in one or more physiological environments in a hospitalized patient (e.g. a patient confined to a hospital bed in situations such as those described in WO 2008042625).

Sensors of the invention can also be incorporated in to a wide variety of medical systems known in the art. Sensors of the invention can be used, for example, in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Certain embodiments of the invention measure peroxide and have the advantageous characteristic of being suited for implantation in a variety of sites in the mammal including regions of subcutaneous implantation and intravenous implantation as well as implantation into a variety of non-vascular regions. A peroxide sensor design that allows implantation into the non-vascular regions has advantages over certain sensor apparatus designs that measure oxygen due to the problems with oxygen noise that can occur in oxygen sensors implanted into the non-vascular regions. For example, in such implanted oxygen sensor apparatus designs, oxygen noise at the reference sensor can compromise the signal to noise ratio which consequently perturbs their ability to obtain stable glucose readings in this environment. The sensors of the invention therefore overcome the difficulties observed with such oxygen sensors in non-vascular regions.

Certain sensor embodiments of the invention further include advantageous long term or "permanent" sensors that are suitable for implantation in a mammal for a time period of greater than 30 days. In particular, as is known in the art (see, e.g., ISO 10993, Biological Evaluation of Medical Devices) medical devices such as the sensors described herein can be categorized into three groups based on implant duration: (1) "Limited" (<24 hours), "Prolonged" (24 hours-30 days), and (3) "Permanent" (>30 days). In some embodiments of the invention, the design of the peroxide sensor of the invention allows for a "Permanent" implantation according to this categorization (i.e., >30 days). In related embodiments of the invention, the highly stable design of the peroxide sensor of the invention allows for an implanted sensor to continue to function in this regard for 2, 3, 4, 5, 6 or 12 months.

Typically, the analyte sensor apparatus includes an analyte sensing layer disposed on the wire at least the working electrode area of the sensor, typically covering a portion or all of the electrode. This analyte sensing layer detectably alters the electrical current at the working electrode in the wire in the presence of an analyte to be sensed. As disclosed herein, this analyte sensing layer typically includes an enzyme or antibody molecule or the like that reacts with the analyte of interest in a manner that changes the concentrations of a molecule that can modulate the current at the working electrode (see e.g. oxygen and/or hydrogen peroxide as shown in the reaction scheme of FIG. 1). Illustrative analyte sensing layers comprise an enzyme such as glucose oxidase (e.g. for use in glucose sensors) or lactate oxidase (e.g. for use in lactate sensors). In some embodiments of the invention, the analyte sensing layer is disposed upon a porous metallic and/or ceramic and/or polymeric matrix with this combination of elements functioning as an electrode in the sensor. In certain embodiments of the invention that require a robust design (e.g. long-term sensors), a ceramic base is used as a dielectric (rather than a polyimide) due to its relatively stronger material properties.

Typically, the analyte-sensing layer further comprises a carrier protein in a substantially fixed ratio with the analyte sensing compound (e.g. the enzyme) and the analyte sensing compound and the carrier protein are distributed in a substantially uniform manner throughout the analyte sensing layer. Typically the analyte sensing layer is very thin, for example, less than 1, 0.5, 0.25 or 0.1 microns in thickness. While not being bound by a specific scientific theory, it is believed that sensors having such thin analyte sensing layers have surprisingly enhanced characteristics as compared to the thicker layers that are typically generated by electrodeposition because electrodeposition produces 3-5 micron thick enzyme layers in which only a fraction of the reactive enzyme within the coating layer is able to access the analyte to be sensed. Such thicker glucose oxidase pellets that are produced by electrodeposition protocols are further observed to have a poor mechanical stability (e.g. a tendency to crack) and further take a longer time to prepare for actual use, typically taking weeks of testing before it is ready for implantation. As these problems are not observed with the thin layered enzyme coatings described herein, these thin coatings are typical embodiments of the invention.

Optionally, the analyte sensing layer has a protein layer disposed thereon and which is typically between this analyte sensing layer and the analyte modulating layer. A protein within the protein layer is an albumin selected from the group consisting of bovine serum albumin and human serum albumin. Typically this protein is crosslinked. Without being bound by a specific scientific theory, it is believed that this separate protein layer enhances sensor function and provides surprising functional benefits by acting as a sort of capacitor that diminishes sensor noise (e.g. spurious background signals). For example, in the sensors of the invention, some amount of moisture may form under the analyte modulating membrane layer of the sensor, the layer which regulates the amount of analyte that can contact the enzyme of the analyte sensing layer. This moisture may create a compressible layer that shifts within the sensor as a patient using the sensor moves. Such shifting of layers within the sensor may alter the way that an analyte such as glucose moves through the analyte sensing layers in a manner that is independent of actual physiological analyte concentrations, thereby generating noise. In this context, the protein layer may act as a capacitor by protecting an enzyme such as GOx from contacting the moisture layer. This protein layer may confer a number of additional advantages such as promoting the adhesion between the analyte sensing layer and the analyte modulating membrane layer. Alternatively, the presence of this layer may result in a greater diffusion path for molecules such as hydrogen peroxide, thereby localizing it to the electrode sensing element and contributing to an enhanced sensor sensitivity.

Typically, the analyte sensing layer and/or the protein layer disposed on the analyte sensing layer has an adhesion promoting layer disposed thereon. Such adhesion promoting layers promote the adhesion between the analyte sensing layer and a proximal layer, typically an analyte modulating layer. This adhesion promoting layer typically comprises a silane compound such as γ-aminopropyltrimethoxysilane which is selected for its ability to promote optimized adhesion between the various sensor layers and functions to stabilize the sensor. Interestingly, sensors having such a silane containing adhesion promoting layers exhibit unexpected properties including an enhanced overall stability. In addition, silane containing adhesion promoting layers provide a number of advantageous characteristics in addition to an ability to enhancing sensor stability, and can, for example, play a beneficial role in interference rejection as well as in controlling the mass transfer of one or more desired analytes.

In certain embodiments of the invention, the adhesion promoting layer further comprises one or more compounds that can also be present in an adjacent layer such as the polydimethyl siloxane (PDMS) compounds that serves to limit the diffusion of analytes such as glucose through the analyte modulating layer. The addition of PDMS to the adhesion promoting layer for example can be advantageous in contexts where it diminishes the possibility of holes or gaps occurring in the adhesion promoting layer as the sensor is manufactured.

Typically the adhesion promoting layer has an analyte modulating layer disposed thereon which functions to modulate the diffusion of analytes therethrough. In one embodiment, the analyte modulating layer includes compositions (e.g. polymers and the like) which serve to enhance the diffusion of analytes (e.g. oxygen) through the sensor layers and consequently function to enrich analyte concentrations in the analyte sensing layer. Alternatively, the analyte modulating layer includes compositions which serve to limit the diffusion of analytes (e.g. glucose) through the sensor layers and consequently function to limit analyte concentrations in the analyte sensing layer. An illustrative example of this is a hydrophilic glucose limiting membrane (i.e. functions to limit the diffusion of glucose therethrough) comprising a polymer such as polydimethyl siloxane or the like. In certain embodiments of the invention, the analyte modulating layer comprises a hydrophilic comb-copolymer having a central chain and a plurality of side chains coupled to the central chain, wherein at least one side chain comprises a silicone moiety.

II. Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A. General Methods for Making Analyte Sensors

A typical embodiment of the invention disclosed herein is a method of making a sensor apparatus for implantation within a mammal comprising the steps of: providing a plurality of wires oriented in a substantially common direction, extruding an electrically insulating cover layer on the wires; removing a portion of the insulating cover layer on each of the wires to provide electrode areas (typically a working electrode, a reference electrode, and a counter electrode); forming an analyte sensing layer on the wire at the working electrode area, wherein the analyte sensing layer includes a composition that can alter the electrical current at the electrode area on the wire in the presence of an analyte; optionally forming a protein layer on the analyte sensing layer; forming an adhesion promoting layer on the analyte sensing layer or the optional protein layer; and forming an analyte modulating layer disposed on the adhesion promoting layer, wherein the analyte modulating layer includes a composition that modulates the diffusion of the analyte therethrough.

As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

B. Typical Protocols and Materials Useful in the Manufacture of Analyte Sensors The disclosure provided herein includes sensors and sensor designs that can be generated using combinations of various well known techniques.

The sensors of the present invention are generally prepared by extruding an electrically insulating cover layer over a plurality of wires that are oriented in substantially the same direction. The insulation may be removed to create electrode areas on each of the wires by a number of suitable methods. These include, for example, laser ablation, mechanical removal and chemical stripping. Alternatively, a selective coating process may be used during the extrusion of the insulating cover layer that allows the cover layer to adhere to the wires except at the electrode areas.

The disclosure further provides for modification of the surface area of the wire at the electrode areas, for example by electroplating, powder deposition or sputtering. Mechanical/geometrical modification may also be used, such as laser micromachining and ion beam etching.

The disclosure further provides methods for applying very thin enzyme coatings to these types of sensors as well as sensors produced by such processes. Methods for producing the extremely thin enzyme coatings of the invention include spin coating processes, dip and dry processes, low shear spraying processes, ink jet printing processes, silk screen processes and the like. As artisans can readily determine the thickness of an enzyme coat applied by process of the art, they can readily identify those methods capable of generating the extremely thin coatings of the invention. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes. Consequently, yet another embodiment of the invention is a method of avoiding the electrodeposition influenced cracking and/or delamination of a coating on a sensor comprising applying the coating via a spin coating process.

Some embodiments of the present invention include an analyte modulating layer deposited over the enzyme-containing layer. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. It has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein. Examples of these nonsiloxane-siloxane copolymers include, but are not limited to, dimethylsiloxane-alkene oxide, tetramethyldisiloxane-divinylbenzene, tetramethyldisiloxane-ethylene, dimethylsiloxane-silphenylene, dimethylsiloxane-silphenylene oxide, dimethylsiloxane-a-methylstyrene, dimethylsiloxane-bisphenol A carbonate copolymers, or suitable combinations thereof. The percent by weight of the nonsiloxane component of the copolymer can be preselected to any useful value but typically this proportion lies in the range of about 40-80 wt %. Among the copolymers listed above, the dimethylsiloxane-bisphenol A carbonate copolymer which comprises 50-55 wt % of the nonsiloxane component is typical. These materials may be purchased from Petrarch Systems, Bristol, Pa. (USA) and are described in this company's products catalog. Other materials which may serve as analyte limiting membrane layers include, but are not limited to, polyurethanes, cellulose acetate, cellulose nitrate, silicone rubber, or combinations of these materials including the siloxane nonsiloxane copolymer, where compatible.

In some embodiments of the invention, the sensor is made by methods which apply an analyte modulating layer that comprises a hydrophilic membrane coating which can regulate the amount of analyte that can contact the enzyme of the sensor layer. For example, a glucose limiting membrane may be used, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g. Kodak AQ), hydrogels or any other membrane known to those skilled in the art that is suitable for such purposes. In certain embodiments of the invention, the analyte modulating layer comprises a hydrophilic comb-copolymer having a central chain and a plurality of side chains coupled to the central chain, wherein at least one side chain comprises a silicone moiety. In some embodiments of the invention pertaining to sensors having hydrogen peroxide recycling capabilities, the membrane layer that is disposed on the glucose oxidase enzyme layer functions to inhibit the release of hydrogen peroxide into the environment in which the sensor is placed and to facilitate the contact between the hydrogen peroxide molecules and the electrode sensing elements.

In some embodiments of the methods of invention, an adhesion promoter layer is disposed between an analyte modulating layer and a analyte sensing layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art. Typically, the adhesion promoter layer comprises a silane compound such as γ-aminopropyltrimethoxysilane. In certain embodiments of the invention, the adhesion promoting layer and/or the analyte modulating layer comprises an agent selected for its ability to crosslink a siloxane moiety present in a proximal. In other embodiments of the invention, the adhesion promoting layer and/or the analyte modulating layer comprises an agent selected for its ability to crosslink an amine or carboxyl moiety of a protein present in a proximal layer. In an optional embodiment, the AP layer further comprises Polydimethyl Siloxane (PDMS), a polymer typically present in analyte modulating layers such as a glucose limiting membrane. In illustrative embodiments the formulation comprises 0.5-20% PDMS, typically 5-15% PDMS, and most typically 10% PDMS. The addition of PDMS to the AP layer can be advantageous in contexts where it diminishes the possibility of holes or gaps occurring in the AP layer as the sensor is manufactured.

As noted above, a coupling reagent commonly used for promoting adhesion between sensor layers is γ-aminopropyltrimethoxysilane. The silane compound is usually mixed with a suitable solvent to form a liquid mixture. The liquid mixture can then be applied or established on the wafer or planar sensing device by any number of ways including, but not limited to, spin-coating, dip-coating, spray-coating, and microdispensing. The microdispensing process can be carried out as an automated process in which microspots of material are dispensed at multiple preselected areas of the device. In addition, photolithographic techniques such as "lift-off" or using a photoresist cap may be used to localize and define the geometry of the resulting permselective film (i.e. a film having a selective permeability). Solvents suitable for use in forming the silane mixtures include aqueous as well as water-miscible organic solvents, and mixtures thereof. Alcoholic water-miscible organic solvents and aqueous mixtures thereof are particularly useful. These solvent mixtures may further comprise nonionic surfactants, such as polyethylene glycols (PEG) having a for example a molecular weight in the range of about 200 to about 6,000. The addition of these surfactants to the liquid mixtures, at a concentration of about 0.005 to about 0.2 g/dL of the mixture, aids in planarizing the resulting thin films. Also, plasma treatment of the wafer surface prior to the application of the silane reagent can provide a modified surface which promotes a more planar established layer. Water-immiscible organic solvents may also be used in preparing solutions of the silane compound. Examples of these organic solvents include, but are not limited to, diphenylether, benzene, toluene, methylene chloride, dichloroethane, trichloroethane, tetrachloroethane, chlorobenzene, dichlorobenzene, or mixtures thereof. When protic solvents or mixtures thereof are used, the water eventually causes hydrolysis of the alkoxy groups to yield organosilicon hydroxides (especially when n=1) which condense to form poly(organosiloxanes). These hydrolyzed silane reagents are also able to condense with polar groups, such as hydroxyls, which may be present on the substrate surface. When aprotic solvents are used, atmospheric moisture may be sufficient to hydrolyze the alkoxy groups present initially on the silane reagent. The R' group of the silane compound (where n=1 or 2) is chosen to be functionally compatible with the additional layers which are subsequently applied. The R' group usually contains a terminal amine group useful for the covalent attachment of an enzyme to the substrate surface (a compound, such as glutaraldehyde, for example, may be used as a linking agent as described by Murakami, T. et al., Analytical Letters 1986, 19, 1973-86).

Like certain other coating layers of the sensor, the adhesion promoter layer can be subjected to one or more suitable radiation and/or chemical and/or heat curing steps as are known in the art. In alternative embodiments, the enzyme layer can be sufficiently crosslinked or otherwise prepared to allow the membrane layer to be disposed in direct contact with the analyte sensing layer in the absence of an adhesion promoter layer.

An illustrative embodiment of the invention is a method of making a sensor by providing several wires with extruded insulative coating layer, where portions of the coating layers have been removed to form electrode areas, spin coating an enzyme layer on the electrode area of at least the working electrode wire, and then forming an analyte contacting layer (e.g. an analyte modulating layer such as a glucose limiting membrane) on the sensor, wherein the analyte contacting layer regulates the amount of analyte that can contact the enzyme layer. In some methods, the enzyme layer is vapor crosslinked on the electrode area. In a typical embodiment of the invention, the electrode areas include at least one working electrode and at least one counter electrode. In certain embodiments, the enzyme layer is formed on at least a portion of the working electrode and at least a portion of the counter electrode. Typically, the enzyme layer that is formed on the sensor is less than 2, 1, 0.5, 0.25 or 0.1 microns in thickness. Typically, the enzyme layer comprises one or more enzymes such as glucose oxidase, glucose dehydrogenase, lactate oxidase, hexokinase or lactate dehydrogenase and/or like enzymes. In a specific method, the enzyme layer comprises glucose oxidase that is stabilized by coating it on the sensor layer in combination with a carrier protein in a fixed ratio. Typically the carrier protein is albumin. Typically such methods include the step of forming an adhesion promoter layer disposed between the glucose oxidase layer and the analyte contacting layer. Optionally, the adhesion promoter layer is subjected to a curing process prior to the formation of the analyte contacting layer.

A number of sensors may be made using the above process, followed by singulation of the individual sensors, by laser or mechanical methods. Then the tips of the wires may be coated to prevent exposure of the wire tips to analyte causing noise. A polyp-xylylene) polymer such as Polypyrrole or other similar coatings may be used.

I. Methods for Using Analyte Sensor Apparatus of the Invention

Related embodiments of the invention is a method of sensing an analyte within the body of a mammal, the method comprising implanting an analyte sensor embodiment disclosed herein in to the mammal, for example by inserting the sensor into the skin of the mammal/patient, and then sensing one or more electrical fluctuations such as alteration in current at the working electrode and correlating the alteration in current with the presence of the analyte, so that the analyte is sensed. Typically the analyte sensor is polarized anodically such that the working electrode where the alteration in current is sensed is an anode. In one such method, the analyte sensor apparatus senses glucose in the mammal. In an alternative method, the analyte sensor apparatus senses lactate, potassium, calcium, oxygen, pH, and/or any physiologically relevant analyte in the mammal.

Certain analyte sensors having the structure discussed above have a number of highly desirable characteristics, which allow for a variety of methods for sensing analytes in a mammal. For example in such methods, the analyte sensor apparatus implanted in the mammal functions to sense an analyte within the body of a mammal for more than 1, 2, 3, 4, 5, or 6 months. Typically, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example in both vascular and non-vascular spaces.

In further embodiments of the invention, a method is disclosed for avoiding tissue trauma at a sensor insertion site by inserting a wired sensor according to the present invention. As discussed above, the wired sensor according the present invention can be smaller and less unobtrusive than layered sensors. In certain embodiments, a needle is used to insert the sensor. The needle is preferably in contact with the sensor, and the needle and sensor are inserted together. Then the needle is removed, leaving the sensor in the patient. To decrease trauma further, a needleless insertion may be used according to the present invention as discussed herein. Inserting the sensor without a needle avoids any trauma that would occur from using the actual needle and results in a very small insertion point. The mounting base discussed above may also be used in connection with insertion methods such that the sensor's signals may be sent to a monitor, transmitter, or other electronics.

IV. Kits and Sensor Sets of the Invention

In further embodiments of the invention In another embodiment of the invention, a kit and/or sensor set, useful for the sensing an analyte as is described above, is provided. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. In some embodiments, the container holds a porous matrix that is coated with a layer of an enzyme such as glucose oxidase. The kit and/or sensor set may further include other materials desirable from a commercial and user standpoint, including elements or devices designed to facilitate the introduction of the sensor into the analyte environment, other buffers, diluents, filters, needles, syringes, and package inserts with instructions for use.

Various publication citations are referenced throughout the specification. In addition, certain text from related art is reproduced herein to more clearly delineate the various embodiments of the invention. The disclosures of all citations in the specification are expressly incorporated herein by reference.

What is claimed is:

1. An analyte sensor comprising:
a plurality of sensor wires having a first end and second end and each arranged in a substantially common orientation, the plurality of sensor wires being electrically conductive and including:
a first sensor wire substantially covered by a first electrically insulating cover, wherein an aperture in the first electrically insulating cover defines a working electrode area;
a second sensor wire substantially covered by a second electrically insulating cover, wherein an aperture in the second electrically insulating cover defines a reference electrode area; and
a third sensor wire substantially covered by a third electrically insulating cover, wherein an aperture in the third electrically insulating cover defines a counter electrode area; wherein:
the plurality of sensor wires has a first side and a second side opposite to the first side, and wherein the working electrode area is only on the first side and the counter electrode area and reference electrode areas are only on the second side; and
the portion of the first wire exposed at the working electrode area is coated with an analyte sensing layer comprising glucose oxidase.

2. The analyte sensor of claim 1 wherein the plurality of sensor wires further includes a fourth sensor wire substantially covered by a fourth electrically insulating cover, wherein an aperture in the fourth electrically insulating cover defines a second working electrode.

3. The analyte sensor of claim 1, wherein the plurality of sensor wires are arranged in a ribbon wire configuration.

4. The analyte sensor of claim 1, wherein the plurality of sensor wires are arranged in a bundled configuration.

5. The analyte sensor of claim 1, wherein the plurality of sensor wires are arranged in a stacked configuration.

6. The analyte sensor of claim 1, wherein the plurality of sensor wires coil around a core cylindrical material.

7. The analyte sensor of claim 6, wherein the core cylindrical material is a material selected from the group consisting of a coated polymer, a hydrogel and a shape memory alloy.

8. The analyte sensor of claim 1, wherein the first and third sensor wires each comprise a material independently selected from the group consisting of platinum, iridium, iridium oxide, and palladium.

9. The analyte sensor of claim 1, wherein the second sensor wire comprises a material selected from the group consisting of silver, silver chloride and a combination of silver and silver chloride.

10. The analyte sensor of claim 1 wherein the first electrically insulating cover, second electrically insulating cover, and third electrically insulating cover each comprise a material independently selected from the group consisting of PTFE (polytetrafluoroethylene), ETFE (ethylene tetrafluoroethylene), FEP (fluorinated ethylene propylene), and PFA (perfluoroalkoxy).

11. The analyte sensor of claim 1 wherein at least one of the plurality of sensor wires comprises a shape memory alloy.

12. The analyte sensor of claim 1, wherein the portion of the first sensor wire exposed at the working electrode area is coated with an electrode coating selected from the group consisting of platinum black, porous platinum, iridium, iridium oxide, and polypyrrole.

13. The analyte sensor of claim 1, wherein the portion of the first sensor wire exposed at the working electrode area has been modified to increase surface area.

14. The analyte sensor of claim 13, wherein the portion of the first sensor wire exposed at the working electrode area has been at least partially coated with one or more components selected from the group consisting of porous metals and porous polymers.

15. The analyte sensor of claim 1, wherein the analyte sensing layer is coated with an analyte modulating layer comprising polydimethyl siloxane (PDMS).

16. The analyte sensor of claim 15, wherein the analyte sensing layer is coated with an adhesion promoting layer that is under the analyte modulating layer, wherein the adhesion promoting layer comprises a silane compound.

17. The analyte sensor of claim 1, wherein at least one of the plurality of sensor wires has a second aperture in its electrically insulating cover defining a second electrode area.

18. The analyte sensor of claim 1, wherein each of the plurality of sensor wires has a tip at the first end of the plurality of sensor wires, wherein the tips are not covered by the electrically insulating covers, and wherein the tips are coated with a poly(p-xylylene) polymer.

19. The analyte sensor of claim 1, wherein each of the plurality of sensor wires is exposed from the electrically insulating cover at a portion defining a contact in electrical communication with the electrode area on that wire, wherein the contacts are substantially near or at the second end of the plurality of sensor wires and the electrode areas are substantially near or at the first end of the plurality of sensor wires.

20. A method for avoiding tissue trauma at a sensor insertion site, comprising:
inserting an analyte sensor into the skin of a patient, wherein the analyte sensor includes: a plurality of sensor wires having a first end and second end and each arranged in a substantially common orientation, the plurality of sensor wires being electrically conductive and including:
a first sensor wire substantially covered by a first electrically insulating cover, wherein an aperture in the first electrically insulating cover defines a working electrode area;
a second sensor wire substantially covered by a second electrically insulating cover, wherein an aperture in the second electrically insulating cover defines a reference electrode area; and
a third sensor wire substantially covered by a third electrically insulating cover, wherein an aperture in the third electrically insulating cover defines a counter electrode area; wherein:
the plurality of sensor wires has a first side and a second side opposite to the first side, and wherein the working electrode area is only on the first side and the counter electrode area and reference electrode areas are only on the second side; and
the portion of the first wire exposed at the working electrode area is coated with an analyte sensing layer comprising glucose oxidase.

21. The method of claim 20, wherein the inserting of the analyte sensor includes:
inserting a needle into the skin of the patient, wherein the needle is in contact with the analyte sensor; and removing the needle from the skin of the patient such that the sensor remains in the skin of the patient.

22. The method of claim 20, wherein the inserting of the analyte sensor is accomplished without a needle.

23. The method of claim 20, further comprising:
placing a mounting base onto the skin of the patient, the mounting base including an opening and a connector portion, wherein the analyte sensor is housed in the mounting base, wherein at least the first end of the analyte sensor extends out of the opening in the mounting base into the skin of the patient substantially at an angle of ninety degrees from the base.

* * * * *